(12) United States Patent
Choi et al.

(10) Patent No.: US 8,507,148 B2
(45) Date of Patent: *Aug. 13, 2013

(54) BENZOXAZINE-BASED MONOMER, POLYMER THEREOF, ELECTRODE FOR FUEL CELL INCLUDING THE POLYMER, ELECTROLYTE MEMBRANE FOR FUEL CELL INCLUDING THE POLYMER, AND FUEL CELL USING THE ELECTRODE

(75) Inventors: Seongwoo Choi, Yongin-si (KR); Jungock Park, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/464,517

(22) Filed: May 4, 2012

(65) Prior Publication Data
US 2012/0251920 A1 Oct. 4, 2012

Related U.S. Application Data

(62) Division of application No. 12/266,039, filed on Nov. 6, 2008, now Pat. No. 8,187,766.

(30) Foreign Application Priority Data

Nov. 6, 2007 (KR) ............... 2007-112750
Oct. 10, 2008 (KR) ............... 2008-99549

(51) Int. Cl.
*H01M 8/10* (2006.01)
*H01M 4/90* (2006.01)
*C07D 265/12* (2006.01)
*C08G 73/06* (2006.01)

(52) U.S. Cl.
USPC ........... 429/492; 429/530; 528/402; 528/423; 544/89; 544/90

(58) Field of Classification Search
USPC ............... 544/89, 90, 92, 93; 429/492, 530; 528/402, 422, 423
See application file for complete search history.

(56) References Cited

U.S. PATENT DOCUMENTS

| | | |
|---|---|---|
| 4,828,699 A | 5/1989 | Soehngen |
| 5,098,985 A | 3/1992 | Harris et al. |
| 5,250,633 A | 10/1993 | Calundann et al. |
| 5,410,012 A | 4/1995 | Connell et al. |
| 5,637,670 A | 6/1997 | Connell et al. |

(Continued)

FOREIGN PATENT DOCUMENTS

| | | |
|---|---|---|
| CN | 101220153 | 7/2008 |
| DE | 2034 887 | 1/1972 |

(Continued)

OTHER PUBLICATIONS

U.S. Office Action dated Jun. 22, 2009, issued in corresponding U.S. Appl. No. 11/947,011.

(Continued)

*Primary Examiner* — Stephen J. Kalafut
(74) *Attorney, Agent, or Firm* — Stein IP, LLC

(57) ABSTRACT

A benzoxazine-based monomer includes a halogen atom-containing functional group and a nitrogen-containing heterocyclic group. A polymer formed from the benzoxazine-based monomer may be used in an electrode for a fuel cell and electrolyte membrane for a fuel cell.

26 Claims, 20 Drawing Sheets

(56) References Cited

U.S. PATENT DOCUMENTS

| | | | |
|---|---|---|---|
| 5,945,233 | A | 8/1999 | Onorato et al. |
| 6,042,968 | A | 3/2000 | Onorato et al. |
| 6,482,946 | B1 | 11/2002 | Dettloff et al. |
| 6,620,905 | B1 | 9/2003 | Musa |
| 6,855,674 | B2 | 2/2005 | Gutierrez |
| 7,094,490 | B2 | 8/2006 | Cao et al. |
| 7,157,509 | B2 | 1/2007 | Li et al. |
| 7,371,480 | B2 | 5/2008 | Ono et al. |
| 7,388,035 | B2 | 6/2008 | Kim et al. |
| 7,405,021 | B2 | 7/2008 | Gascoyne et al. |
| 7,510,678 | B2 | 3/2009 | Kim et al. |
| 7,619,044 | B2 | 11/2009 | Lee et al. |
| 7,649,025 | B2 | 1/2010 | Kitamura et al. |
| 7,709,579 | B2 | 5/2010 | Lehmann et al. |
| 8,119,307 | B2 * | 2/2012 | Choi et al. ............... 429/524 |
| 8,187,766 | B2 * | 5/2012 | Choi et al. ............ 429/530 X |
| 2001/0041283 | A1 | 11/2001 | Hitomi |
| 2002/0127474 | A1 | 9/2002 | Fleischer et al. |
| 2002/0164516 | A1 | 11/2002 | Hasegawa et al. |
| 2003/0190516 | A1 | 10/2003 | Tanno |
| 2004/0005493 | A1 | 1/2004 | Tanno |
| 2004/0028976 | A1 | 2/2004 | Cabasso et al. |
| 2004/0206953 | A1 | 10/2004 | Morena et al. |
| 2004/0231143 | A1 | 11/2004 | Visco et al. |
| 2004/0241522 | A1 | 12/2004 | Ono et al. |
| 2004/0261660 | A1 | 12/2004 | Li et al. |
| 2005/0074651 | A1 | 4/2005 | Kidai et al. |
| 2005/0084728 | A1 | 4/2005 | Kim et al. |
| 2005/0089744 | A1 | 4/2005 | Kim et al. |
| 2005/0130006 | A1 | 6/2005 | Hoshi et al. |
| 2005/0142413 | A1 | 6/2005 | Kimura et al. |
| 2005/0247908 | A1 | 11/2005 | Keller et al. |
| 2006/0078774 | A1 | 4/2006 | Uensal et al. |
| 2006/0241192 | A1 | 10/2006 | Kitamura et al. |
| 2007/0020507 | A1 | 1/2007 | Kim et al. |
| 2007/0141426 | A1 | 6/2007 | Choi et al. |
| 2007/0184323 | A1 | 8/2007 | Lee et al. |
| 2007/0200994 | A1 | 8/2007 | Yanagisawa |
| 2007/0238723 | A1 | 10/2007 | Goble et al. |
| 2007/0275285 | A1 | 11/2007 | Choi et al. |
| 2008/0020264 | A1 | 1/2008 | Sun et al. |
| 2008/0045688 | A1 | 2/2008 | Lin et al. |
| 2008/0050633 | A1 | 2/2008 | Kwon et al. |
| 2008/0118817 | A1 | 5/2008 | Lee et al. |
| 2008/0145743 | A1 | 6/2008 | Choi et al. |
| 2008/0157422 | A1 | 7/2008 | Lee et al. |
| 2009/0075147 | A1 | 3/2009 | Kitamura et al. |
| 2009/0117436 | A1 | 5/2009 | Choi et al. |
| 2009/0117440 | A1 | 5/2009 | Choi et al. |
| 2010/0273087 | A1 | 10/2010 | Choi et al. |
| 2011/0189581 | A1 | 8/2011 | Choi et al. |

FOREIGN PATENT DOCUMENTS

| | | |
|---|---|---|
| DE | 603 02 673 | 8/2006 |
| EP | 1 247 844 | 10/2002 |
| EP | 1 253 661 | 10/2002 |
| EP | 1 760 110 | 3/2007 |
| EP | 1 881 549 | 1/2008 |
| JP | 10-25343 | 1/1998 |
| JP | 11-503262 | 3/1999 |
| JP | 11-97011 | 4/1999 |
| JP | 2001-19844 | 1/2001 |
| JP | 2001-270891 | 10/2001 |
| JP | 2001-271070 | 10/2001 |
| JP | 2002-260682 | 9/2002 |
| JP | 2003-12747 | 1/2003 |
| JP | 2003-12924 | 1/2003 |
| JP | 2003-286320 | 10/2003 |
| JP | 2003-327694 | 11/2003 |
| JP | 2004-43547 | 2/2004 |
| JP | 2004-103494 | 4/2004 |
| JP | 2004-149779 | 5/2004 |
| JP | 2004-179514 | 6/2004 |
| JP | 2005-41936 | 2/2005 |
| JP | 2005-82690 | 3/2005 |
| JP | 2005-283082 | 10/2005 |
| JP | 2006-339065 | 12/2006 |
| JP | 2007-70631 | 3/2007 |
| JP | 2007-214108 | 8/2007 |
| KR | 10-2006-0011831 | 2/2006 |
| KR | 10-2006-0055291 | 5/2006 |
| KR | 10-2007-0025626 | 3/2007 |
| KR | 10-2007-0025627 | 3/2007 |
| KR | 10-0745741 | 7/2007 |
| KR | 10-2007-0102579 | 10/2007 |
| WO | WO 96/13872 | 5/1996 |
| WO | WO 02/14334 | 2/2002 |
| WO | WO 02/057279 | 7/2002 |
| WO | WO 03/072638 | 9/2003 |
| WO | WO 2004/009708 | 1/2004 |
| WO | WO 2004/101509 | 11/2004 |
| WO | WO 2005/000955 | 1/2005 |
| WO | WO 2006/132207 | 12/2006 |

OTHER PUBLICATIONS

U.S. Office Action dated Sep. 3, 2009, issued in corresponding U.S. Appl. No. 11/743,778.
U.S. Office Action dated Sep. 8, 2009, issued in corresponding U.S. Appl. No. 11/765,033.
U.S. Office Action dated Jun. 1, 2010, issued in corresponding U.S. Appl. No. 11/765,056.
U.S. Office Action dated Jan. 8, 2010, issued in corresponding U.S. Appl. No. 11/514,254.
U.S. Office Action dated Jan. 15, 2010, issued in corresponding U.S. Appl. No. 11/947,011.
U.S. Office Action dated Feb. 19, 2010, issued in corresponding U.S. Appl. No. 11/743,778.
U.S. Office Action dated Mar. 30, 2010, issued in corresponding U.S. Appl. No. 11/947,011.
U.S. Office Action dated May 6, 2010, issued in corresponding U.S. Appl. No. 11/514,254.
U.S. Office Action dated Jun. 17, 2010, issued in corresponding U.S. Appl. No. 11/765,033.
U.S. Office Action dated Jul. 11, 2011, issued in corresponding U.S. Appl. No. 12/208,492.
U.S. Office Action dated Aug. 11, 2011, issued in corresponding U.S. Appl. No. 12/247,338.
U.S. Office Action dated Aug. 18, 2011, issued in corresponding U.S. Appl. No. 12/266,039.
U.S. Office Action dated Sep. 2, 2011, issued in corresponding U.S. Appl. No. 12/262,854.
U.S. Office Action dated Sep. 12, 2011, issued in corresponding U.S. Appl. No. 12/263,011.
U.S. Office Action dated Nov. 14, 2011, issued in corresponding U.S. Appl. No. 12/208,492.
U.S. Office Action dated Dec. 12, 2011, issued in corresponding U.S. Appl. No. 12/263,011.
U.S. Office Action dated Dec. 22, 2011, issued in corresponding U.S. Appl. No. 12/247,338.
U.S. Office Action dated Jan. 20, 2012, issued in corresponding U.S. Appl. No. 11/947,011.
U.S. Notice of Allowance dated Jan. 31, 2012, issued in corresponding U.S. Appl. No. 12/266,039.
U.S. Office Action dated Feb. 2, 2012, issued in corresponding U.S. Appl. No. 12/208,664.
U.S. Notice of Allowance dated Feb. 3, 2012, issued in corresponding U.S. Appl. No. 12/208,492.
U.S. Notice of Allowance dated Feb. 3, 2012, issued in corresponding U.S. Appl. No. 12/262,854.
U.S. Notice of Allowance dated Mar. 14, 2012, issued in corresponding U.S. Appl. No. 12/263,011.
U.S. Notice of Allowability dated Mar. 22, 2012, issued in corresponding U.S. Appl. No. 12/263,011.
U.S. Office Action dated Apr. 26, 2012, issued in corresponding U.S. Appl. No. 11/947,011.
U.S. Office Action dated May 10, 2012, issued in corresponding U.S. Appl. No. 12/247,338.
U.S. Notice of Allowance dated Jul. 11, 2012, issued in corresponding U.S. Appl. No. 12/247,338.

Seong-Woo Choi et al., "*Synthesis, characterization and thermal degradation of functional benzoxazine monomers and polymers containing phenylphosphine oxide*", Polymer Degradation and Stability 91 (2006), pp. 1166-1178.
Seong-Woo Choi, et al., Polybenzoxazine Based Membrane with Enhanced Oxygen Permeability Inducing Fluorine Containing Benzoxazine Monomer as an Electrode Additive and Binder for High Temperature PEM Fuel Cells; slides of presentation at 212th ECS, Washington, DC, Oct. 9, 2007.
STN Registry database entries for RN 35141-82-3, RN 35141-83-4 and RN 35141-84-5, Database entry date Nov. 16, 1984. Accessed Jan. 26, 2012.
Tarek AGAG, Journal of Applied Polymer Science, vol. 100, pp. 3769-3777 (2006).
212th ECS Meeting—Washington DC, Oct. 7-12, 2007, Program Information, B10—Proton Exchange Membrane Fuel Cells (PEMFC 7) Energy Technology/Physical and Analytical Electrochemistry/Battery/Industrial Electrochemistry and Electrochemical Engineering.
B. Antalek. "Using Pulsed Gradient Spin Echo NMR for Chemical Mixture Analysis: How to Obtain Optimum Results.", Concepts in Magnetic Resonance (2002) vol. 14(4), pp. 225-258.
S. Viel et al. "Diffusion-Ordered NMR Spectroscopy: A Versatile Tool for the Molecular Weight Determination of Uncharged Polysaccharides.", Biomacromolecules (2003) vol. 4, pp. 1843-1847.
D. A. Jayawickrama et al. "Polymer additives mixture analysis using pulsed-field gradient NMR spectroscopy.", Magn.Reson. Chem (1998), vol. 36, pp. 755-760.
K. Nishinari et al. "Soulution Properties of Pullulan.", Macromolecules (1991) vol. 24, pp. 5590-5593.
L.C. Van Gorkom et al. "Analysis of DOSY and GPC-NMR Experiments on Polymers by Multivariate Curve Resolution.", Journal of Magnetic Resonance (1998) vol. 130, pp. 125-130.
A. Chen et al. "Determination of Molecular Weight Distributions for Polymers by Diffusion-Ordered NMR.", J. Am. Chem. Soc. (1995) vol. 117, pp. 7965-7970.
Hajime Kimura et al. "Epoxy Resin Cured by Bisphenol a Based Benzoxazine.", Journal of Applied Polymer Science (1998), vol. 68, pp. 1903-1910.
Schuster, Martin F.H., et al., "Anhydrous Proton-Conducting Polymers", Annu. Rev. Mater. Res., vol. 33, 2003, pp. 233-261.
Yamada, M. et al., "Anhydrous proton conducting polymer electrolytes based on poly(vinylphosphonic acid)-heterocyclic composite material", Polymer, vol. 46, No. 9, 2005, pp. 2986-2992.
Pu, H., et al., "Proton Transport in Polybenzimidazole Blended with $H_3PO_4$ or $H_2SO_4$", J. Polymer Science, Part B: Polymer Physics, vol. 40, 2002, pp. 663-669.
Kim, Hyoung-Juhn et al. *Polybenzimidazoles for High Temperature Fuel Cell Applicatio*. Macromol. Rapid Commun. 2004, vol. 25, pp. 1410-1413.
Ueda, Mitsuru et al. *Poly(benzimidazole) Synthesis by Direct Reaction of Methoxyphthalic Acids and Tetramine*. J. Poly. Sci. Part A: Polym. Chem, 27 pp. 2815-2818 (1989).
Choi et al., "Synthesis, characterization and thermal degradation of functional benzoxazine monomers and polymers containing phenylphosphine oxide", Polymer Degradation and Stability, vol. 91, No. 5, May 1, 2006, pp. 1166-1178.
Low, Hong Yee, et al. "Structural Effects of Phenols on the Thermal and Thermo-oxidative Degradation of Polybenzoxazines". Polymer, vol. 40, No. 15. Jul. 1999. pp. 4365-4376.
Kim, H.J., et al. "Synthesis and Thermal Characterization of Polybenzoxazines Based on Acetylene-functional Monomers". Polymer, vol. 40, No. 23. Nov. 1999. pp. 6565-6573.
Shen, Shyan Bob, et al. "Synthesis and Characterization of Polyfunctional Naphthoxazines and Related Polymers". Journal of Applied Polymer Science vol. 61, No. 9. 1996, pp. 1595-1605.
Lin et al., "Synthesis and Properties of Flame-Retardant Benzoxazines by Three Approaches", Journal of Polymer Science, Part A: Polymer Chemistry, vol. 44, 2006, pp. 3454-3468.
Hirai et al., "Air-Induced *anti*-Markovnikov Addition of Secondary Phosphine Oxides and H-Phosphinates to Alkenes", National Institute of Advanced Industrial Science and Technology, Organic Letters 2007, vol. 9, No. 1, pp. 53-55.
Beletskaya et al., "Arylation of 6*H*-Dibenzo[c,e][1,2 $\lambda^5$]oxaphosphinine 6-Oxide", Russian Journal of Organic Chemistry, vol. 40, No. 12, 2004, pp. 1782-1786.
Yamada et al., "A Novel Synthesis of 6-Hydroxyalkyl- and 6-Hydroxy-aralkyl-6*H*-dibenz[*c,e*][1,2]oxaphosphorin 6-Oxides", vol. 27, 1990, pp. 845-850.
Human translation of JP 2003-286320, A. Takeichi et al., Oct. 2003.
Human translation of JP 2004-103494, Kimura et al., Apr. 2004.
Machine translation of JP 2004-149779, Sakaguchi et al., May 2004.
European Search Report issued in European Patent Application No. 06254551.2-2115 on Nov. 21, 2006.
European Office Action issued in corresponding European Patent Application No. 07250814.6 on Oct. 30, 2007.
European Search Report issued in European Patent Application No. 08104319.2 on Oct. 13, 2008.
European Search Report issued in European Patent Application No. 08157494.9 on Nov. 24, 2008.
European Office Action dated Dec. 4, 2008, issued in corresponding European Patent Application No. 08164095.5.
European Search Report issued in European Patent Application No. 08164096.3 on Jan. 20, 2009.
European Search Report issued in European Patent Application No. 08166328.8 on Jan. 22, 2009.
European Search Report issued in European Patent Application No. 08168081.1 on Jan. 28, 2009.
Extended European Search Report issued in European Patent Application No. 08168032.4 on Feb. 3, 2009.
Extended European Search Report issued in European Patent Application No. 08168404.5 on Apr. 23, 2009.
European Search Report dated Jul. 21, 2010 issued in corresponding European Patent Application No. 10164784.0.
European Search Report dated Jul. 21, 2010 issued in corresponding European Patent Application No. 10164785.7.
Japanese Office Action issued in Japanese Patent Application No. 2006-239572 on Feb. 17, 2009.
Japanese Office Action dated Jun. 21, 2011, issued in corresponding Japanese Patent Application No. 2007-309320.
Japanese Office Action dated Sep. 20, 2011, issued in corresponding Japanese Patent Application No. 2008-233675.
Japanese Office Action dated Oct. 23, 2011, issued in corresponding Japanese Patent Application No. 2007-309320.
Korean Office Action dated Jul. 21, 2010, issued in corresponding Korean Patent Application No. 10-2008-0089999.
Korean Office Action dated Oct. 6, 2010, issued in corresponding Korean Patent Application No. 10-2008-0099549.
U.S. Appl. No. 11/514,254, filed Sep. 1, 2006, Seong-woo Choi et al., Samsung SDI Co., Ltd.
U.S. Appl. No. 11/514,831, filed Sep. 5, 2006, Seong-woo Choi et al., Samsung SDI Co., Ltd.
U.S. Appl. No. 11/743,778, filed May 3, 2007, Seong-woo Choi et al., Samsung SDI Co., Ltd.
U.S. Appl. No. 11/856,350, filed Sep. 17, 2007, Seong-woo Choi et al., Samsung SDI Co., Ltd.
U.S. Appl. No. 11/947,011, filed Nov. 29, 2007, Seong-woo Choi et al., Samsung Electronics Co., Ltd.
U.S. Appl. No. 12/208,492, filed Sep. 11, 2008, Seong-woo Choi et al., Samsung Electronics Co., Ltd.
U.S. Appl. No. 12/208,664, filed Sep. 11, 2008, Seong-woo Choi et al., Samsung Electronics Co., Ltd.
U.S. Appl. No. 11/765,033, filed Jun. 19, 2007, Hee-young Sun et al., Samsung SDI Co., Ltd.
U.S. Appl. No. 11/765,065, filed Jun. 19, 2007, Kyung-jung Kwon et al., Samsung SDI Co., Ltd.
U.S. Appl. No. 12/247,338, filed Oct. 8, 2008, Seong-woo Choi et al., Samsung Electronics Co., Ltd.
U.S. Appl. No. 12/263,011, filed Oct. 31, 2008, Seong-woo Choi et al., Samsung Electronics Co., Ltd.
U.S. Appl. No. 12/262,854, filed Oct. 31, 2008, Seong-woo Choi et al., Samsung Electronics Co., Ltd.
U.S. Appl. No. 12/266,039, filed Nov. 6, 2008, Seong-woo Choi et al., Samsung Electronics Co., Ltd.
U.S. Appl. No. 13/466,750, filed May 8, 2012, Seong-woo Choi et al., Samsung Electronics Co., Ltd.
U.S. Appl. No. 13/466,843, filed May 8, 2012, Seong-woo Choi et al., Samsung Electronics Co., Ltd.
U.S. Appl. No. 13/478,893, filed May 23, 2012, Seong-woo Choi et al., Samsung Electronics Co., Ltd.
U.S. Appl. No. 13/523,516, filed Jun. 14, 2012, Seong-woo Choi et al., Samsung Electronics Co., Ltd.
U.S. Appl. No. 13/560,321, filed Jul. 27, 2012, Seong-woo Choi et al., Samsung Electronics Co., Ltd.

* cited by examiner

BENZOXAZINE-BASED MONOMER, POLYMER THEREOF, ELECTRODE FOR FUEL CELL INCLUDING THE POLYMER, ELECTROLYTE MEMBRANE FOR FUEL CELL INCLUDING THE POLYMER, AND FUEL CELL USING THE ELECTRODE

CROSS-REFERENCE TO RELATED APPLICATIONS

This is a divisional of U.S. application Ser. No. 12/266,039, filed Nov. 6, 2008, now U.S. Pat. No. 8,187,766 which claims the benefit of Korean Patent Application No. 10-2007-112750, filed on Nov. 6, 2007, and Korean Patent Application No. 10-2008-99549, filed on Oct. 10, 2008, in the Korean Intellectual Property Office, the disclosures of which are incorporated herein by reference.

BACKGROUND OF THE INVENTION

1. Field of the Invention

One or more embodiments of the present invention relate to an electrode for a fuel cell and a fuel cell employing the same.

2. Description of the Related Art

Fuel cells, which use a polymer electrolyte membrane as an electrolyte, operate at a relatively low temperature and can be small in size. Thus, fuel cells may be used as power sources in electric vehicles or distributed generation systems for homes. As a polymer electrolyte membrane used in polymer electrolyte fuel cells, a perfluorocarbonsulfonic acid-based polymer membrane such as NAFION (registered trademark) has been used.

However, such polymer electrolyte membranes typically need water to provide proton conduction abilities, and thus, the polymer electrolyte membranes typically need to be humidified. In addition, to enhance cell system efficiencies, it may be necessary to operate polymer electrolyte membranes at a high temperature of at least 100° C. However, the moisture in polymer electrolyte membranes may evaporate at this temperature, and the polymer electrolyte membranes may not function properly as a solid electrolyte.

To address those problems in the art, non-humidified electrolyte membranes that can operate at a high temperature of at least 100° C. under nonhumidified conditions have been developed. For example, U.S. Pat. No. 5,525,436 discloses polybenzimidazole doped with a phosphoric acid, and the like as a material constituting non-humidified electrolyte membranes.

In addition, in cells that operate at a low temperature, such as cells using a perfluorocarbonsulfonic acid-based polymer membrane, to prevent gas diffusion in electrodes due to water (formation water) that is produced as electricity is generated in an electrode, particularly a cathode, electrodes using polytetrafluoroethylene (PTFE) as a waterproof agent to have hydrophobic properties have been widely used (see, for example, Japanese Patent Laid-Open Publication No. hei 05-283082).

In addition, phosphoric acid type fuel cells operating at a high temperature of 150 to 200° C. use a liquid phosphoric acid as an electrolyte. However, a large amount of the liquid phosphoric acid is present in electrodes, which interferes with gas diffusion. Therefore, an electrode catalyst layer that is formed by adding polytetrafluoroethylene (PTFE) as a waterproof agent to an electrode catalyst, and which can prevent fine pores in electrodes from being clogged by a phosphoric acid, has been used.

In addition, in fuel cells using a polybenzimidazole (PBI) electrolyte membrane, which retains phosphoric acid as a nonhumidified electrolyte at a high temperature, to reduce contact between electrodes and the electrolyte membrane, a method of impregnating electrodes with a liquid phosphoric acid has been tried and a method of increasing a loading amount of metal catalysts has been tried. However, such fuel cells have not exhibited improved properties, and thus there is a need for improvement.

In addition, when air is supplied to a cathode when a solid polymer electrolyte doped with phosphoric acid is used, the fuel cell requires an aging time of about 1 week even if the composition of the cathode is optimized. By supplying oxygen to the cathode instead of air, performances of the cathode can be improved and the aging time can also be reduced. However, the need to supply of oxygen to the cathode is an obstacle in realizing widespread use of the cathode. In addition, a polymer electrolyte membrane formed of PBI typically does not have satisfactory mechanical properties and chemical stability at a high temperature and capability of retaining a phosphoric acid.

SUMMARY OF THE INVENTION

One or more embodiments of the present invention include a benzoxazine-based monomer having excellent thermal resistance and high phosphoric acid resistance, a polymer thereof, an electrode for a fuel cell including the polymer, an electrolyte membrane for a fuel cell including the polymer, and a fuel cell using the electrode.

Additional aspects and/or advantages will be set forth in part in the description which follows and, in part, will be apparent from the description, or may be learned by practice of the invention.

According to an embodiment of the present invention, there is provided a benzoxazine-based monomer represented by Formula 1 below:

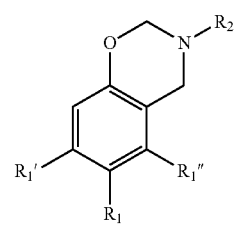

<Formula 1> wherein at least one of $R_1$, $R_1'$, $R_1''$, and $R_2$ is a halogen atom, a halogenated $C_1$-$C_{20}$ alkyl group, a halogenated $C_1$-$C_{20}$ alkoxy group, a halogenated $C_2$-$C_{20}$ alkenyl group, a halogenated $C_2$-$C_{20}$ alkynyl group, a halogenated $C_6$-$C_{20}$ aryl group, a halogenated $C_6$-$C_{20}$ aryloxy group, a halogenated $C_2$-$C_{20}$ heteroaryl group, a halogenated $C_2$-$C_{20}$ heteroaryloxy group, a halogenated $C_4$-$C_{20}$ cycloalkyl group, or a halogenated $C_2$-$C_{20}$ heterocyclic group, another one of $R_1$, $R_1'$, $R_1''$, and $R_2$ is a substituted or unsubstituted non-halogenated $C_2$-$C_{20}$ heterocyclic group and any remaining ones of $R_1$, $R_1'$, $R_1''$, and $R_2$ are hydrogen.

According to an embodiment of the present invention, there is provided a monomer represented by one of Formulae 2 through 5 below:

<Formula 2>

<Formula 3>

<Formula 4>

<Formula 5> wherein $R_2$ is a halogen atom, a halogenated $C_1$-$C_{20}$ alkyl group, a halogenated $C_1$-$C_{20}$ alkoxy group, a halogenated $C_2$-$C_{20}$ alkenyl group, a halogenated $C_2$-$C_{20}$ alkynyl group, a halogenated $C_6$-$C_{20}$ aryl group, a halogenated $C_6$-$C_{20}$ aryloxy group, a halogenated $C_2$-$C_{20}$ heteroaryl group, a halogenated $C_2$-$C_{20}$ heteroaryloxy group, a halogenated $C_4$-$C_{20}$ cycloalkyl group, or a halogenated $C_2$-$C_{20}$ heterocyclic group.

According to an embodiment of the present invention, there is provided a polymer of a benzoxazine-based monomer that is a polymerization product of the benzoxazine-based monomer described above or a polymerization product between the benzoxazine-based monomer described above and a crosslinkable compound.

According to an embodiment of the present invention, there is provided a polymer that is a polymerization product of the monomer represented by one of Formulae 2 through 5 above or a polymerization product between the monomer represented by one of Formulae 2 through 5 above and a crosslinkable compound.

According to an embodiment of the present invention, there is provided an electrode for a fuel cell, the electrode comprising a catalyst layer comprising the polymer of the benzoxazine-based monomer described above or the polymer of the monomer represented by one of Formulae 2 through 5 above.

According to an embodiment of the present invention, there is provided an electrolyte membrane for a fuel cell, comprising the polymer of the benzoxazine-based monomer described above or the polymer of the monomer represented by one of Formulae 2 through 5 above.

According to an embodiment of the present invention, there is provided a fuel cell including the electrode for a fuel cell. An electrolyte membrane in the fuel cell may comprise the polymer of the benzoxazine-based monomer described above or the polymer of the monomer represented by one of Formulae 2 through 5 above.

According to an embodiment of the present invention, there is provided a fuel cell including the electrolyte membrane for a fuel cell.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
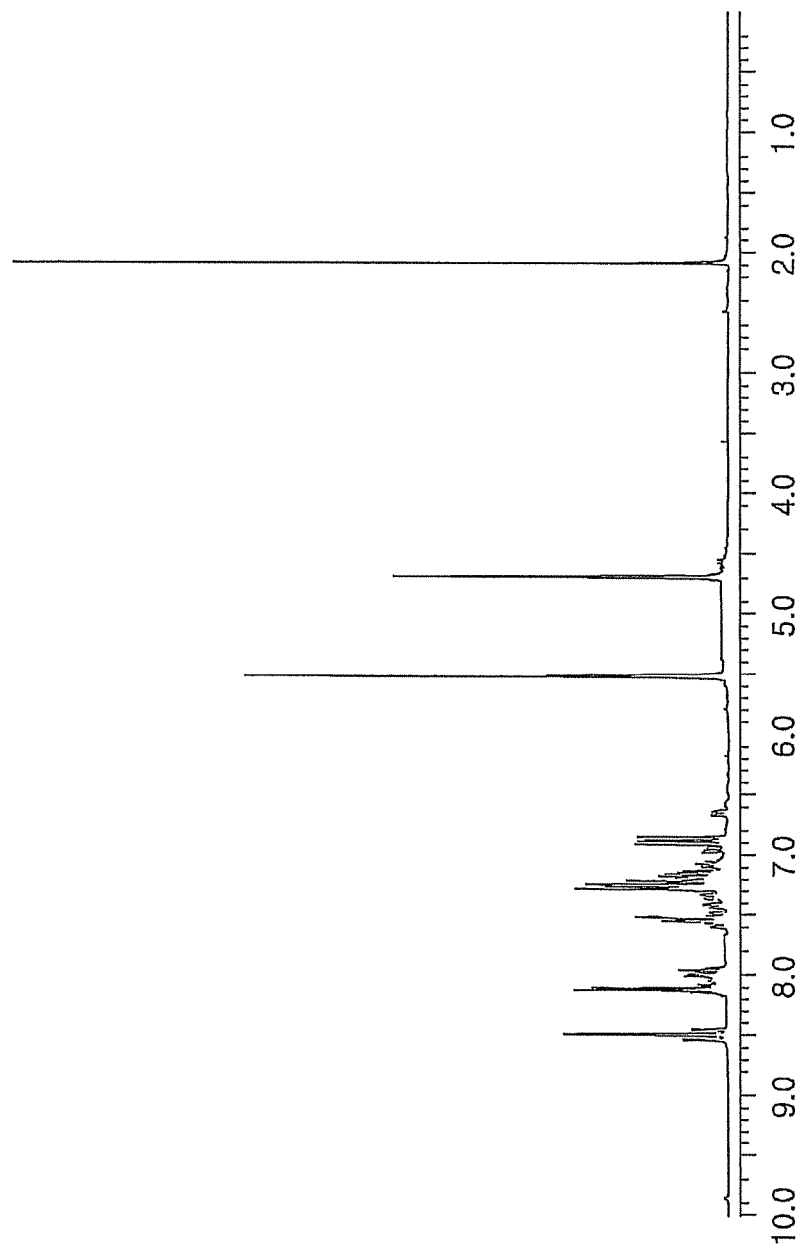
FIGS. 1 through 7 are graphs respectively showing nuclear magnetic resonance (NMR) spectra of benzoxazine-based monomers prepared in Synthesis Examples 1 through 7.

Reference will now be made in detail to embodiments, examples of which are illustrated in the accompanying drawings, wherein like reference numerals refer to the like elements throughout. The embodiments are described below in order to explain the present invention by referring to the figures.

An embodiment of the present invention provides a benzoxazine-based monomer represented by Formula 1 below:

<Formula 1>

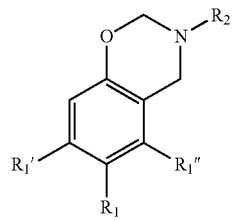

wherein at least one of $R_1$, $R_1'$, $R_1''$, and $R_2$ is a halogen atom, a halogenated $C_1$-$C_{20}$ alkyl group, a halogenated $C_1$-$C_{20}$ alkoxy group, a halogenated $C_2$-$C_{20}$ alkenyl group, a halogenated $C_2$-$C_{20}$ alkynyl group, a halogenated $C_6$-$C_{20}$ aryl group, a halogenated $C_6$-$C_{20}$ aryloxy group, a halogenated $C_2$-$C_{20}$ heteroaryl group, a halogenated $C_2$-$C_{20}$ heteroaryloxy group, a halogenated $C_4$-$C_{20}$ cycloalkyl group, or a halogenated $C_2$-$C_{20}$ heterocyclic group, another one of $R_1$, $R_1'$, $R_1''$, and $R_2$ is a substituted or unsubstituted non-halogenated $C_2$-$C_{20}$ heterocyclic group and any remaining ones of $R_1$, $R_1'$, $R_1''$, and $R_2$ are hydrogen.

The term "halogenated" used in Formula 1 refers to substitution with a halogen atom such as fluorine, chlorine, or iodine.

In Formula 1, as a non-limiting example, at least one of R1, R1', R1", and R2 may be fluorine, a fluorinated C1-C20 alkyl group, a fluorinated C6-C20 aryl group, a fluorinated C2-C20 heteroaryl group, a fluorinated C2-C20 heteroaryloxy group, a fluorinated C4-C20 cycloalkyl group, or a fluorinated C2-C20 heterocyclic group, and the other one of R1, R1', R1", and R2 may be a nitrogen-containing C3-C6 heterocyclic group derived from tertiary amine such as pyridine.

In addition, in Formula 1, as a non-limiting example, the nitrogen-containing C3-C6 heterocyclic group may be one a group represented by one of the following formulae:

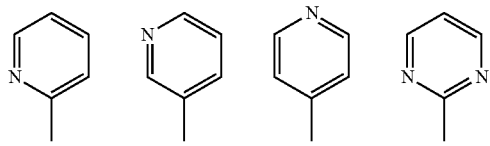

As a non-limiting example, the fluorinated C6-C20 aryl group may be a group represented by one of the following formulae:

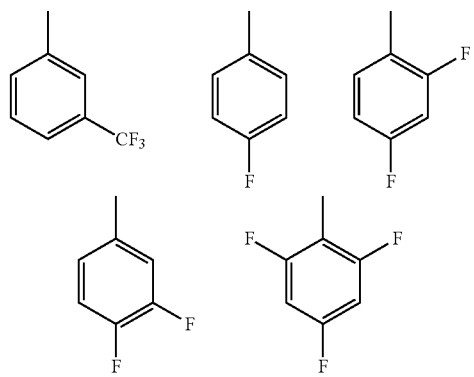

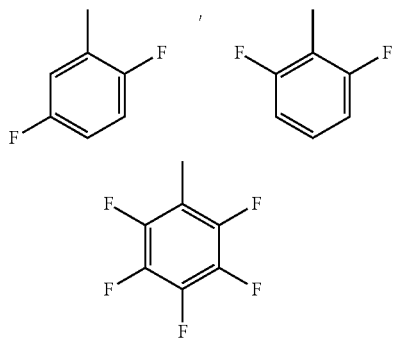

In Formula 1, as a non-limiting example, at least one of R1, R1', and R1" may be fluorine, a fluorinated C1-C20 alkyl group, a fluorinated C6-C20 aryl group, a fluorinated C2-C20 heteroaryl group, a fluorinated C2-C20 heteroaryloxy group, a fluorinated C4-C20 cycloalkyl group, or a fluorinated C2-C20 heterocyclic group, and R2 may be a nitrogen-containing C3-C6 heterocyclic group.

As a non-limiting example, the benzoxazine-based monomer of Formula 1 may a compound represented by one of Formulae 6 through 9:

<Formula 6>

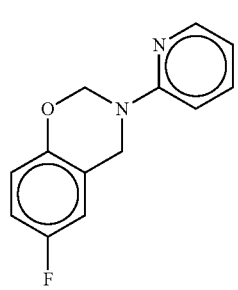

<Formula 7>

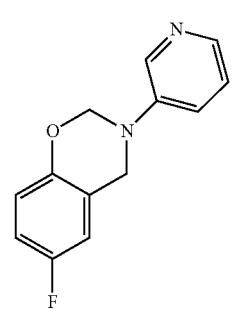

<Formula 8>

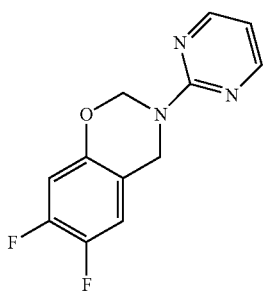

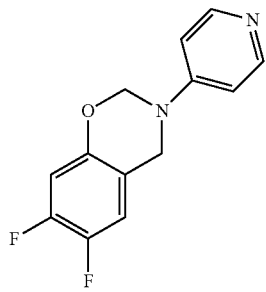

<Formula 9>

An embodiment of the present invention provides a monomer represented by one of Formulae 2 through 5 below:

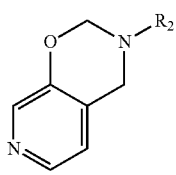

<Formula 2>

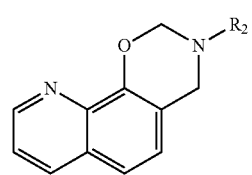

<Formula 3>

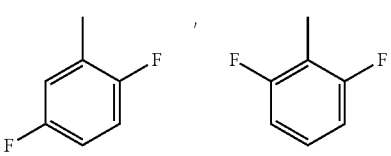

<Formula 4>

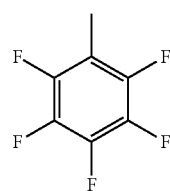

<Formula 5> wherein $R_2$ is a halogen atom, a halogenated $C_1$-$C_{20}$ alkyl group, a halogenated $C_1$-$C_{20}$ alkoxy group, a halogenated $C_2$-$C_{20}$ alkenyl group, a halogenated $C_2$-$C_{20}$ alkynyl group, a halogenated $C_6$-$C_{20}$ aryl group, a halogenated $C_6$-$C_{20}$ aryloxy group, a halogenated $C_2$-$C_{20}$ heteroaryl group, a halogenated $C_2$-$C_{20}$ heteroaryloxy group, a halogenated $C_4$-$C_{20}$ cycloalkyl group, or a halogenated $C_2$-$C_{20}$ heterocyclic group.

As a non-limiting example, $R_2$ may be a group represented by one of the following formulae.

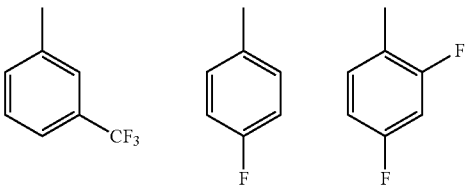

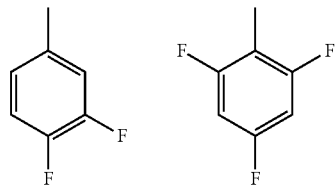

As a non-limiting example, the monomer represented by one of Formulae 2-5 may be a compound represented by one of Formulae 10 through 13 below.

<Formula 10>

<Formula 11>

9
-continued

<Formula 12>

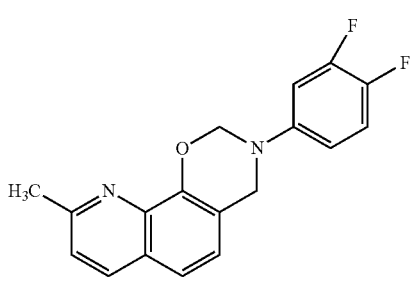

<Formula 13>

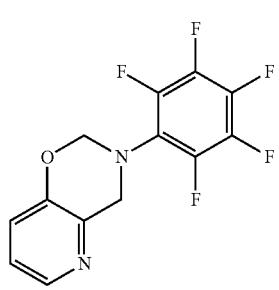

According to an embodiment of the present invention, a polymer of a benzoxazine-based monomer may be obtained by polymerization of the benzoxazine-based monomer described above or by polymerization between the benzoxazine-based monomer described above and a crosslinkable compound. Also, a polymer may be obtained by polymerization of the monomer according to Formulae 2-5, or more specifically, Formulae 10-13 above, or by polymerization between the monomer according to Formulae 2-5 above, or more specifically, Formulae 10-13 above, and a crosslinkable compound.

The benzoxazine-based monomers represented Formulae 6-9 have a fluorine or a fluorine-containing functional group as $R_1$ and a pyridyl group as $R_2$. Due to these structural properties, the benzoxazine-based monomer and a polymer thereof contain the fluorine functional group, thereby having improved oxygen transmission and contain the pyridyl group, thereby having excellent heat resistance and resistance to phosphoric acid.

In addition, the monomers represented by Formulae 10-12 and a polymer thereof have the similar structural properties to those of the benzoxazine-based monomer represented by one of Formulae 6-9. That is, the monomers represented by Formulae 10-12 and a polymer thereof contain a fluorine group, thereby having improved thermal stability at a high temperature and contain a pyridine-based amine structure, thereby having improved capability of retaining acid.

An electrode for a fuel cell according to an embodiment of the present invention includes a catalyst layer comprising the polymer of the benzoxazine-based monomer of Formula 1. The catalyst layer includes a catalyst. The polymer of the benzoxazine-based monomer represented by Formula 1 is used as a binder of the electrode, and in particular, can act as a binder. Thus, a conventional binder is not necessary for the electrode.

The electrode according to aspects of the present invention contains the polymer of the benzoxazine-based monomer as described above, and thus the transmission of oxygen into the electrode is increased, and thermal resistance and resistance to phosphoric acid of the electrode are improved. As a result, doped phosphoric acid can easily be impregnated into the electrode.

10

The benzoxazine-based monomer of Formula 1 may be prepared according to Reaction Scheme 1 below.

Referring to Reaction Scheme 1, the benzoxazine-based monomer of Formula 2 can be prepared by heating a phenol compound (A), p-formaldehyde (B) and an amine compound (C) without a solvent or by adding a solvent to A, B and C and then refluxing the mixture, and thereafter working up the resultant:

<Reaction Scheme 1>

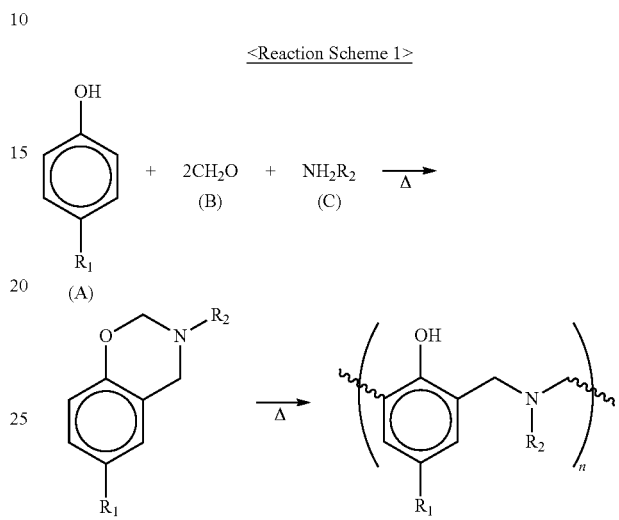

wherein $R_1$ and $R_2$ are the same as defined in Formula 1, and $R_1{}'$ and $R_1{}''$ are each independently hydrogen in the compound of Formula 1 in Reaction Scheme 1.

In the case of adding the solvent to the phenol compound (A), p-formaldehyde (B) and the amine compound (C), the solvent used may be 1,4-dioxane, chloroform, dichloromethane, THF, or the like. The heating temperature is adjusted to be within a range of temperatures at which the solvent used can be refluxed.

The monomer represented by Formulae 2 through 5 and polymers thereof can be prepared in the same manner as in Reaction Scheme 1, except that a hydroxypyridine or hydroxyquinoline compound corresponding to the phenol compound (A) (such as, for example, 3-hydroxypyridine, 4-hydroxypyridine, 5-hydroxypyridine, or the like) may be used.

The electrode for a fuel cell that is obtained according to an embodiment of the present invention contains a polymer of the benzoxazine-based monomer represented by Formula 1 or a polymer of the monomer represented by one of Formulae 2 through 5. The benzoxazine-based monomer of Formula 1 or the monomer represented by one of Formulae 2 through 5 is polymerized during a drying process of a composition for forming an electrode active material layer at a time of the formation of the electrode and/or during a time when a fuel cell including the electrode operates, thereby being converted to the polymer thereof.

When the polymer of the benzoxazine-based monomer represented by Formula 1 or the polymer of the monomer represented by one of Formulae 2 through 5 according to aspects of the present invention is used in forming an electrode for a fuel cell, oxygen transmission is improved even when only air is supplied to the cathode, and wettability of phosphoric acid ($H_3PO_4$) in an electrode and thermal stability can be improved. Therefore, a fuel cell employing the electrode and an electrolyte membrane can operate at a high temperature under nonhumidified conditions, can have enhanced thermal stability, and can exhibit improved electricity generation performance.

The amount of the polymer of the benzoxazine-based monomer represented by Formula 1 or the polymer of the monomer represented by one of Formulae 2 through 5 may be in the range of 0.001 to 0.65 parts by weight, or more specifically, in the range of 0.01 to 0.05 parts by weight based on 1 part by weight of the catalyst.

When the polymer of the benzoxazine-based monomer represented by Formula 1 or the polymer of the monomer represented by one of Formulae 2 through 5 is less than 0.001 parts by weight based on 1 part by weight of the catalyst, wettability of phosphoric acid in an electrode may not be sufficiently improved. On the other hand, when the amount of the polymer of the benzoxazine-based monomer represented by Formula 1 or the polymer of the monomer represented by one of Formulae 2 through 5 is greater than 0.65 parts by weight based on 1 part by weight of the catalyst, flooding of phosphoric acid may be facilitated.

The catalyst may be platinum alone, or an alloy or mixture of platinum and at least one metal selected from the group consisting of gold, palladium, rhodium, iridium, ruthenium, tin, molybdenum, cobalt, and chrome. Alternatively, the catalyst may be a support catalyst in which the catalyst metal is loaded on a carbonaceous support. In particular, the catalyst may be a catalyst metal including at least one of Pt, PtCo, and PtRu, or a support catalyst in which the catalyst metal is loaded on a carbonaceous support.

The electrode may further include a binder such as is typically used in the preparation of an electrode for a fuel cell.

As non-limiting examples, the binder may be at least one selected from the group consisting of polyvinylidenefluoride, polytetrafluoroethylene (PTFE), tetrafluoroethylene-hexafluoropropylene copolymer, and perfluoroethylene. The amount of the binder may be in the range of 0.001 to 0.5 parts by weight based on 1 part by weight of the catalyst. When the amount of the binder is less than 0.001 parts by weight based on 1 part by weight of the catalyst, wettability of phosphoric acid in an electrode may not be sufficiently improved. On the other hand, when the amount of the binder is greater than 0.5 parts by weight based on 1 part by weight of the catalyst, flooding of phosphoric acid may be facilitated.

A method of preparing an electrode for a fuel cell, according to an embodiment of the present invention, will now be described. Although the following description refers to preparing an electrode using the benzoxazine monomer of Formula 1, it is to be understood that an electrode may be prepared by the same method using one of the monomers of Formulae 2 to 5.

First, a catalyst is dispersed in a solvent to obtain a dispersion. The solvent used may be N-methylpyrrolidone (NMP), dimethylformamide (DMAc), or the like, and the amount of the solvent may be in the range of 1 to 10 parts by weight based on 1 part by weight of the catalyst.

A mixture of the benzoxazine-based monomer of Formula 1, a binder, and a solvent is added to the dispersion and mixed together, and then the resultant is stirred.

The mixture may further include a crosslinkable compound, if desired. Examples of the crosslinkable compound include at least one selected from polybenzimidazole (PBI), polybenzimidazole-base complexes, polybenzthiazoles, polybenzoxazoles, and polyimides. The amount of crosslinkable compound may be in the range of 5-95 parts by weight based on 100 parts by weight of the benzoxazine-based monomer of Formula 1.

The solvent may be N-methylpyrrolidone (NMP), dimethylacetamide (DMAc), or the like.

The resultant is coated onto the surface of a carbon support to prepare an electrode. Herein, the carbon support may be fixed on a glass substrate in order to easily coat the resultant thereon. The coating method is not particularly limited, but, may be coating using a doctor blade, bar coating, screen printing, or the like.

The coated resultant is dried at a temperature in the range of 20 to 150° C. to remove the solvent. The drying time is dependent on the drying temperature, and may be in the range of 10 to 60 minutes. As a non-limiting example, the drying process may be performed sequentially at room temperature for 1 hour, at 60° C. for at least 15 minutes, at 80° C. for at least 10 minutes, and at 120° C. for at least 10 minutes.

In addition, the catalyst layer of the electrode may further include at least one proton conductor selected from a phosphoric acid and a $C_1$-$C_{20}$ organic phosphonic acid. The amount of the proton conductor may be in the range of 10 to 1,000 parts by weight based on 100 parts by weight of the total weight of the electrode. The concentration of the acid used is not particularly limited. However, in the case of a phosphoric acid, 85 wt % of an aqueous phosphoric acid solution may be used, and the impregnation time of the phosphoric acid may be in the range of 2.5 to 14 hours at 80° C.

An electrolyte membrane according to an embodiment of the present invention comprises a polymer of benzoxazine-based monomer that is a polymerization product of the benzoxazine-based monomer represented by Formula 1 or a polymer that is a polymerization product of a monomer represented by one of Formulae 2 through 5. Alternatively, the electrolyte membrane according to an embodiment of the present invention may comprise a polymerization product between the benzoxazine-based monomer represented by one of Formula 1 and a crosslinkable compound or a polymerization product of the monomer represented by one of Formulae 2 through 5 and a crosslinkable compound.

The crosslinkable compound may be the same as that described in the formation of the electrode. In particular, examples of the crosslinkable compound include at least one selected from polybenzimidazole (PBI), polybenzimidazole-base complexes, polybenzthiazoles, polybenzoxazoles and polyimides. For example, polybenzimidazole-base complexes are disclosed in Korean Patent No. 2007-102579.

When the crosslinkable compound is polybenzimidazole or a polybenzimidazole-base complex, the electrolyte membrane comprises a crosslinked product of a polybenzoxazine-based compound which is obtained by curing a thermosetting resin, polybenzoxazine with a thermoplastic resin, polybenzimidazole or a polybenzimidazole-base complex.

In addition, as described above, the electrolyte membrane comprises the crosslinked product of a polybenzoxazine-based compound which is a polymerization product between the benzoxazine-based monomer of Formula 1 and a crosslinkable compound, and thus problems occurring when an electrolyte membrane formed of polybenzimidazole alone is used, for example, a pin-hole phenomenon caused by deficient mechanical and chemical stabilities at a high temperature can be addressed. In addition, when the electrode includes a polymer of a halogen-containing benzoxazine-based monomer, in particular, a fluorine-containing benzoxazine-based monomer, as described above, the transmission of oxygen into the electrode increases and the amount of dissolved oxygen in the electrode increases, and thus activation time is decreased. The same advantages may be obtained when a polymerization product between a monomer of Formulae 2 through 5 and a crosslinkable compound is used.

A fuel cell according to an embodiment of the present invention comprises an optimized electrolyte membrane forming material and/or electrode forming material, thereby having maximized cell performance.

Hereinafter, an electrolyte membrane and a method of preparing the electrolyte membrane according to an embodiment of the present invention will be described. When an electrolyte membrane is prepared only using the benzoxazine-based monomer of Formula 1, the preparation process is the same as those described herein, except that the crosslinkable compound was not used. Similarly, it is to be understood that an electrolyte membrane may be prepared by the same method described herein using one of the monomers of Formulae 2 to 5 instead of the benzoxazine-based monomer of Formula 1.

As a first method, the benzoxazine-based monomer represented by Formula 1 is blended with a crosslinkable compound, and the mixture is cured at a temperature in the range of 50 to 250° C., and preferably 80 to 220° C. The cured mixture is impregnated with a proton conductor such as an acid to prepare an electrolyte membrane.

The amount of the crosslinkable compound may be in the range of 5 to 95 parts by weight based on 100 parts by weight of the benzoxazine-based monomer of Formula 1.

When the amount of the crosslinkable compound is less than 5 parts by weight based on 100 parts by weight of the benzoxazine-based monomer of Formula 1, the electrolyte membrane may not be impregnated with a phosphoric acid, and thus, proton conductivity of the electrolyte membrane may be reduced. On the other hand, when the amount of the crosslinkable compound is greater than 95 parts by weight based on 100 parts by weight of the benzoxazine-based monomer of Formula 1, the crosslinked object may be partially dissolved in polyphosphoric acid due to the presence of excessive phosphoric acid.

As a second method, an electrolyte membrane is formed using a mixture of the benzoxazine-based monomer represented by Formula 1 and a crosslinkable compound.

The formation of the electrolyte membrane may be performed by a tape casting method, or a conventional coating method. The conventional coating method may be a method in which the mixture is cast onto a support using a doctor blade. For example, a doctor blade with a 250 to 500 µm gap may be used.

When the casting method using a doctor blade is used, the process of forming the electrolyte membrane further includes separating the electrolyte membrane from the support, after the time when curing of the mixture occurs and before the time when impregnation of the resultant with acid occurs. To perform the process of separating the electrolyte membrane from the support, the mixture is immersed in distilled water with a temperature in the range of 60 to 80° C.

The support can be any support that can support an electrolyte membrane, such as, for example, a glass substrate, a polyimide film, and the like. When the tape casting method is used, a tape cast membrane is separated from a support such as polyethyleneterephthalate before being cured, and then is put into an oven.

In addition, when a membrane is formed by the tape casting method using a mixture of a benzoxazine-based monomer and polybenzimidazole, a process of filtering the mixture may be further performed.

The tape cast membrane is cured by heat treatment, and then is impregnated with a proton conductor such as acid to form an electrolyte membrane.

Non-limiting examples of the proton conductor include a phosphoric acid, a phosphonic acid, a $C_1$-$C_{20}$ organic phosphonic acid, and the like. As non-limiting examples, the $C_1$-$C_{20}$ organic phosphonic acid may be ethyl phosphonic acid or methyl phosphonic acid.

The amount of the proton conductor may be in the range of 300 to 1,000 parts by weight based on 100 parts by weight of the total weight of the electrolyte membrane. The concentration of the acid used is not particularly limited. However, in the case of a phosphoric acid, 85 wt % of an aqueous phosphoric acid solution may be used, and the impregnation time of the phosphoric acid may be in the range of 2.5 to 14 hours at 80° C.

A method of preparing a fuel cell using the electrode for a fuel cell according to an embodiment of the present invention will now be described.

Any electrolyte membrane that is commonly used in the preparation of fuel cells can be used herein. For example, the electrolyte membrane that is commonly used in a fuel cell may be a polybenzimidazole electrolyte membrane, a polybenzoxazine-polybenzimidazole copolymer electrolyte membrane, a polytetrafluoroethylene (PTFE) porous membrane, or the like.

Alternatively, an electrolyte membrane including a crosslinked product of polybenzoxazine-based compounds that is prepared by polymerization of the benzoxazine-based monomer represented by Formula 1 and a crosslinkable compound can also be used. Alternatively, an electrolyte membrane including the crosslinked product of a monomer represented by one of Formulae 2 through 5 and a crosslinkable compound may be used.

In particular, when the electrolyte membrane including the crosslinked product of polybenzoxazine-based compounds according to an embodiment of the present invention is used, contact resistance between the electrode and electrolyte membrane is decreased due to an improvement in compatibility, and thus cell performance of the fuel cell can be maximized.

A method of manufacturing a membrane-electrode assembly for a fuel cell is as follows. The term "membrane and electrode assembly (MEA)" used herein refers to a structure in which electrodes, each comprising a catalyst layer and a diffusion layer, are deposited on respective surfaces of the electrolyte membrane.

The MEA may be formed by positioning the electrodes including the catalyst layer described above at respective sides of the electrolyte membrane prepared by the process described above, joining them together at a high temperature and a high pressure, and then joining a fuel diffusion layer to the catalyst layers.

As a non-limiting example, the joining may be performed under a pressure in the range of 0.1 to 3 ton/cm², and particularly about 1 ton/cm², in a state reached when the MEA is heated up to a temperature that softens the electrolyte membrane.

Next, a bipolar plate is disposed on each side of the membrane-electrode assembly to manufacture a fuel cell. Typically, the bipolar plate has grooves used for supplying fuel, and functions as a current collector.

The use of the fuel cell according to aspects of the present invention is not particularly limited. For example, the fuel cell may be used as a polymer electrolyte membrane (PEM) fuel cell.

The substituents used herein are defined as follows.

Non-limiting examples of the $C_1$-$C_{20}$ alkyl group include methyl, ethyl, propyl, isobutyl, sec-butyl, pentyl, iso-amyl, hexyl, or the like. The $C_1$-$C_{20}$ alkyl group may be unsubstituted or at least one hydrogen atom of the alkyl group may be substituted with a halogen atom, a $C_1$-$C_{20}$ alkyl group substituted with a halogen atom (for example, $CCF_3$, $CHCF_2$, CH$_2$F, CCl$_3$, and the like), a hydroxyl group, a nitro group, a cyano group, an amino group, an amidino group, hydrazine, hydrazone, a carboxyl group or a salt thereof, a sulfonic acid group or a salt thereof, a phosphoric acid or a salt thereof, a C$_1$-C$_{20}$ alkyl group, a C$_2$-C$_{20}$ alkenyl group, a C$_2$-C$_{20}$ alkynyl group, a C$_1$-C$_{20}$ heteroalkyl group, a C$_6$-C$_{20}$ aryl group, a C$_6$-C$_{20}$ arylalkyl group, a C$_6$-C$_{20}$ heteroaryl group, a C$_1$-C$_{20}$ heterocyclic group, or a C$_6$-C$_{20}$ heteroarylalkyl group.

Non-limiting examples of the alkoxy group include methoxy, ethoxy, or propoxy. The alkoxy group may be unsubstituted or at least one hydrogen atom of the alkoxy group may be substituted with a substituent described above with respect to the alkyl group.

Non-limiting examples of the C$_2$-C$_{20}$ alkenyl group include vinylene, allylene, or the like. The C$_2$-C$_{20}$ alkenyl group may be unsubstituted or at least one hydrogen atom of the alkenyl group may be substituted with a substituent described above with respect to the alkyl group.

Non-limiting examples of the C$_2$-C$_{20}$ alkynyl group include acetylene, or the like. The C$_2$-C$_{20}$ alkynyl group may be unsubstituted or at least one hydrogen atom of the alkynyl group may be substituted with a substituent described above with respect to the alkyl group.

The term "aryl group" used herein refers to a C$_6$-C$_{20}$ carbocyclic aromatic system containing at least one ring, wherein the rings can be pendantly attached to each other or fused with each other. The term "aryl," which may be used alone or in combination with other terms, refers to an aromatic radical such as, for example, phenyl, naphthyl, tetrahydronaphthyl, or the like. The aryl group may be unsubstituted or may have a substituent such as haloalkylene, nitro, cyano, alkoxy and lower alkylamino. For example, at least one hydrogen atom of the aryl group may be substituted with a substituent described above with respect to the alkyl group.

Non-limiting examples of the aryloxy group include phenoxy. The aryloxy group may be unsubstituted or at least one hydrogen atom of the aryloxy group may be substituted with a substituent as described above with respect to the alkyl group.

The term "heteroaryl group" used herein refers to a monovalent monocyclic or bicyclic aromatic bivalent organic compound that contains 1, 2 or 3 hetero atoms selected from the group consisting of N, O, P, and S, and has 1 to 20 carbon atoms. The heteroaryl group may be unsubstituted or at least one hydrogen atom of the heteroaryl group may be substituted with a substituent as described above with respect to the alkyl group.

The term "cycloalkyl group" used herein refers to a C$_5$-C$_{10}$ cyclic group such as a cyclohexyl group. The cycloalkyl group may be unsubstituted or at least one hydrogen atom of the cycloalkyl group may be substituted with a substituent as described above with respect to alkyl group.

The term "heterocyclic group" used herein refers to a 5 to 10 membered group containing a hetero atom such as nitrogen, sulfur, phosphorus, oxygen, and the like, and may be pyridyl, or the like, as a non-limiting example. The heterocyclic group may be unsubstituted or at least one hydrogen atom of the heterocyclic group may be substituted with a substituent as described above with respect to the alkyl group.

According to an embodiment of the present invention, the electrode for a fuel cell with reduced activation time and improved voltage performance according to current density and the electrolyte membrane for a fuel cell with excellent thermal stability at a high temperature and excellent capability of retaining acid can be prepared.

Hereinafter, aspects of the present invention will be described more specifically with reference to the following examples. The following examples are only for illustrative purposes and are not intended to limit the scope of the invention.

SYNTHESIS EXAMPLE 1

Preparation of 4FPh-2AP of Formula 6

2 g of 4-fluorophenol (17.8 mmol), 1.24 g of para-formaldehyde (39.3 mmol), and 1.85 g of 2-aminopyridine (19.6 mmol) were sequentially added to a 100 ml one-neck round bottomed flask, and then mixed in an oil bath at 90° C.

The reaction mixture was transparent in an early stage of the reaction, and about 30 minutes after the reaction, the reaction mixture converted into a dark brown material in the form of a transparent gel. The reaction mixture was quenched with tetrahydrofurane (THF) and cooled to room temperature.

The crude product cooled to room temperature was base washed twice by solvent extraction that used an aqueous 1N NaOH solution, and then washed once again with deionized water.

After the washing process was terminated, the organic layer was dried using MgSO$_4$, and then continuously filtered. A solvent was removed from the filtrate using a rotary evaporator, and then the purified product was dried in a vacuum oven at 40° C. for 6 hours.

The structure of 4FPh-2AP of Formula 6 was confirmed by nuclear magnetic resonance (NMR) spectroscopy performed using a Varian Unity INOVA600 spectrometer at 600 MHz, and the results are shown in FIG. 1.

SYNTHESIS EXAMPLE 2

Preparation of 4FPh-3AP of Formula 7

A target material was prepared in the same manner as in Synthesis Example 1, except that 3-aminopyridine was used instead of 2-aminopyridine.

Figure 2:
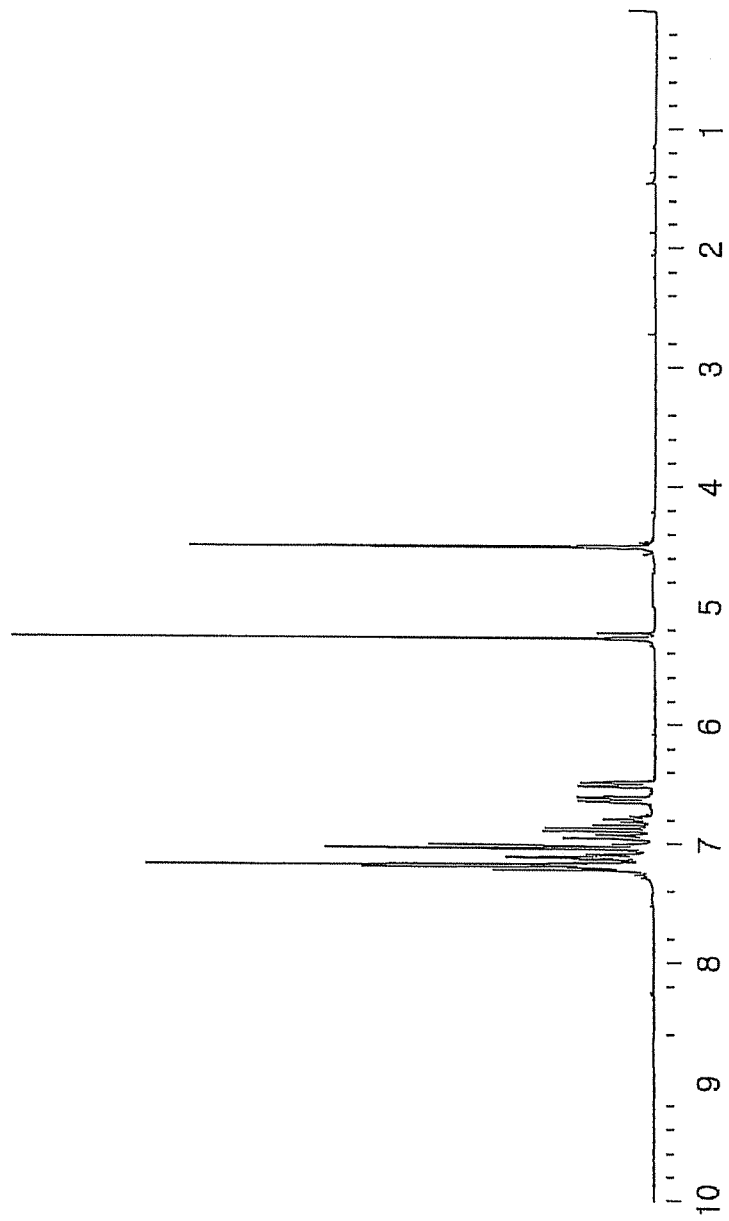

The structure of 4FPh-3AP of Formula 7 was confirmed by NMR spectroscopy performed using a Varian Unity INOVA600 spectrometer at 600 MHz, and the results are shown in FIG. 2.

SYNTHESIS EXAMPLE 3

Preparation of 34DFph2APMD of Formula 8

3.93 g of 3,4-difluorophenol (30 mmol), 1.98 g of para-formaldehyde (66 mmol), and 3.14 g of 2-aminopyridine (33 mmol) were sequentially added to a 100 ml one-neck round bottomed flask, and then mixed in an oil bath at 90° C.

The reaction mixture was transparent in an early stage of the reaction, and about 30 minutes after the reaction, the reaction mixture converted into a dark brown material in the form of a transparent gel. The reaction mixture was quenched with tetrahydrofurane (THF) and cooled to room temperature.

The crude product cooled to room temperature was base washed twice by solvent extraction that used an aqueous 1N NaOH solution, and then washed once again with deionized water.

After the washing process was terminated, the organic layer was dried using MgSO$_4$, and then continuously filtered. A solvent was removed from the filtrate using a rotary evaporator, and then the purified product was dried in a vacuum oven at 40° C. for 6 hours.

Figure 3:
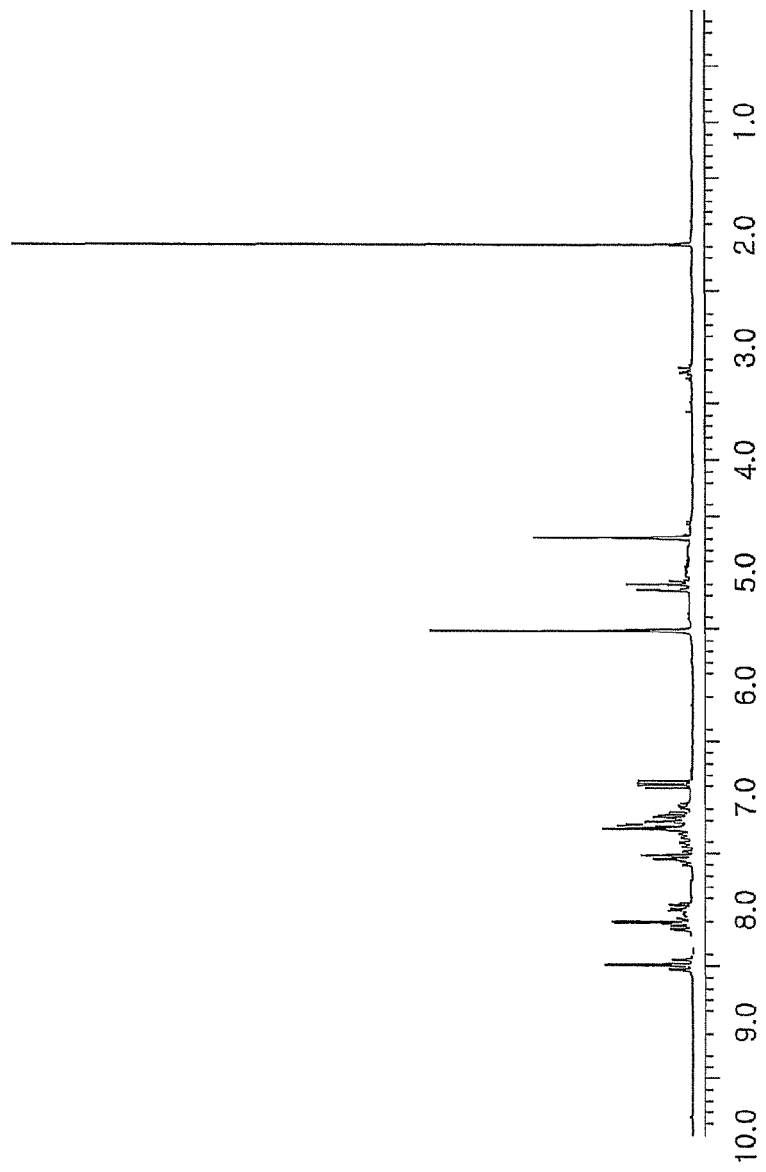

The structure of 34DFph2APMD of Formula 8 was confirmed by NMR spectroscopy performed using a Varian Unity INOVA600 spectrometer at 600 MHz, and the results are shown in FIG. 3.

SYNTHESIS EXAMPLE 4

Preparation of 34DFph4AP of Formula 9

A target material was prepared in the same manner as in Synthesis Example 3, except that 3.1 g of 4-aminopyridine (33 mmol) was used instead of 3.14 g of 2-aminopyridine (33 mmol).

Figure 4:
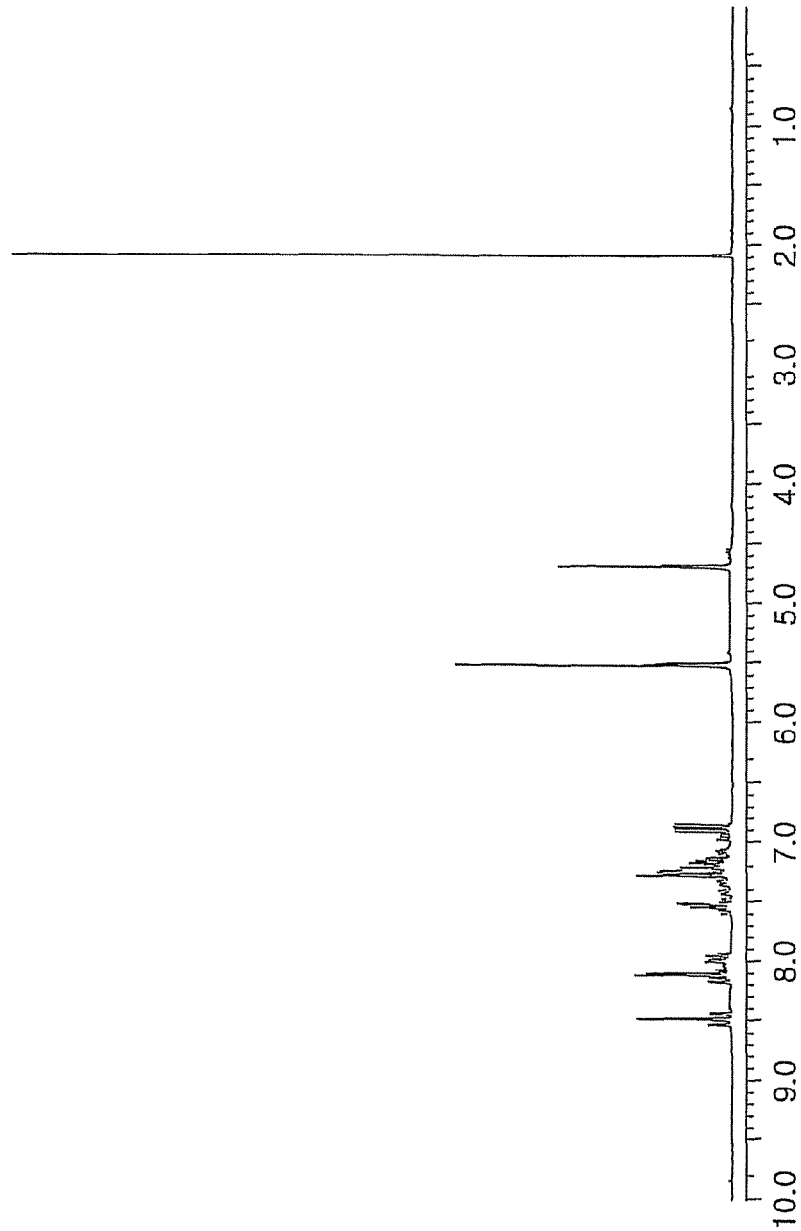

The structure of 34DFph4AP of Formula 9 was confirmed by NMR spectroscopy performed using a Varian Unity INOVA600 spectrometer at 600 MHz, and the results are shown in FIG. 4.

SYNTHESIS EXAMPLE 5

Preparation of 3HP-34DFA of Formula 10

A target material was prepared in the same manner as in Synthesis Example 1, except that 2 g of 3-hydroxypyridine (21 mmol), 1.46 g of para-formaldehyde (46.3 mmol), and 2.98 g of 3,4-difluoroaniline (23.1 mmol) were added to a 100 ml one-neck round bottomed flask.

Figure 5:
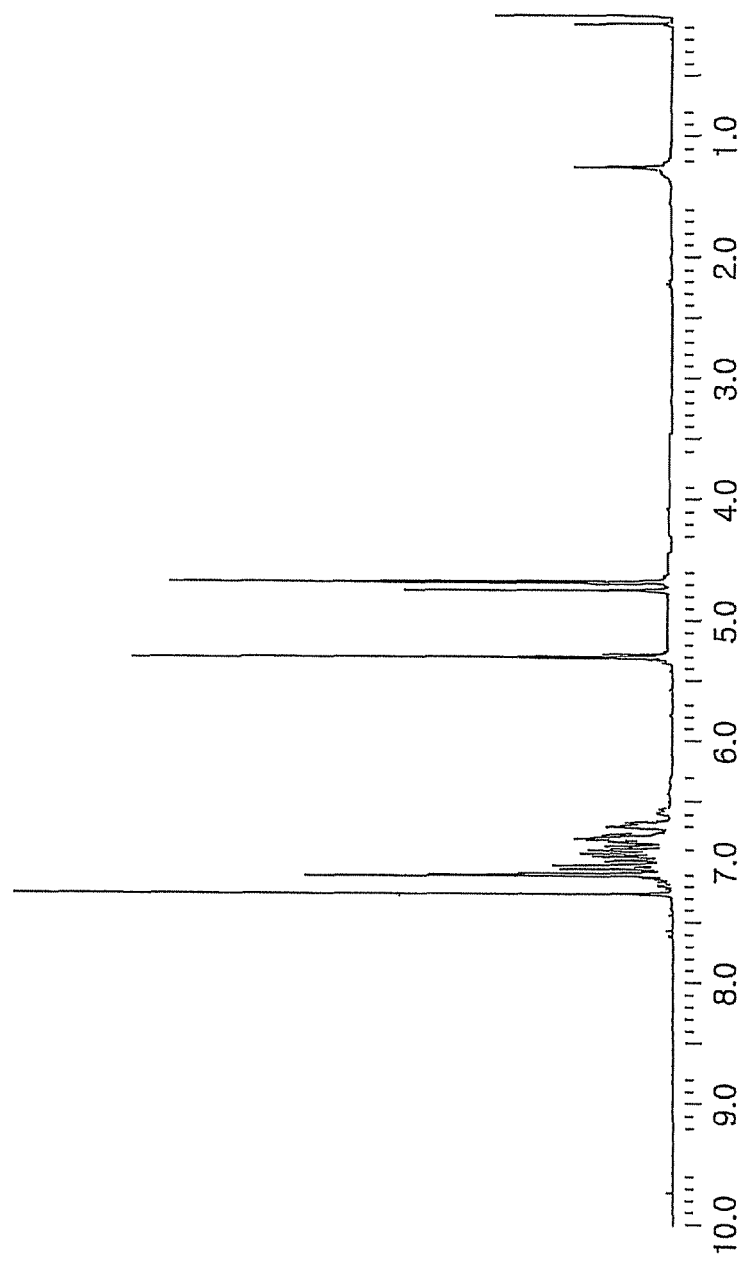

The structure of 3HP-34DFA of Formula 10 was confirmed by NMR spectroscopy performed using a Varian Unity INOVA600 spectrometer at 600 MHz, and the results are shown in FIG. 5.

SYNTHESIS EXAMPLE 6

Preparation of 8HQ-34DFA of Formula 11

A target material was prepared in the same manner as in Synthesis Example 5, except that an alcohol represented by the following formula was used instead of 2 g of 3-hydroxypyridine (21 mmol).

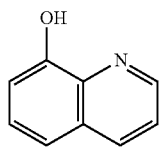 [SMILES: Oc1cccc2cccnc12]

Figure 6:
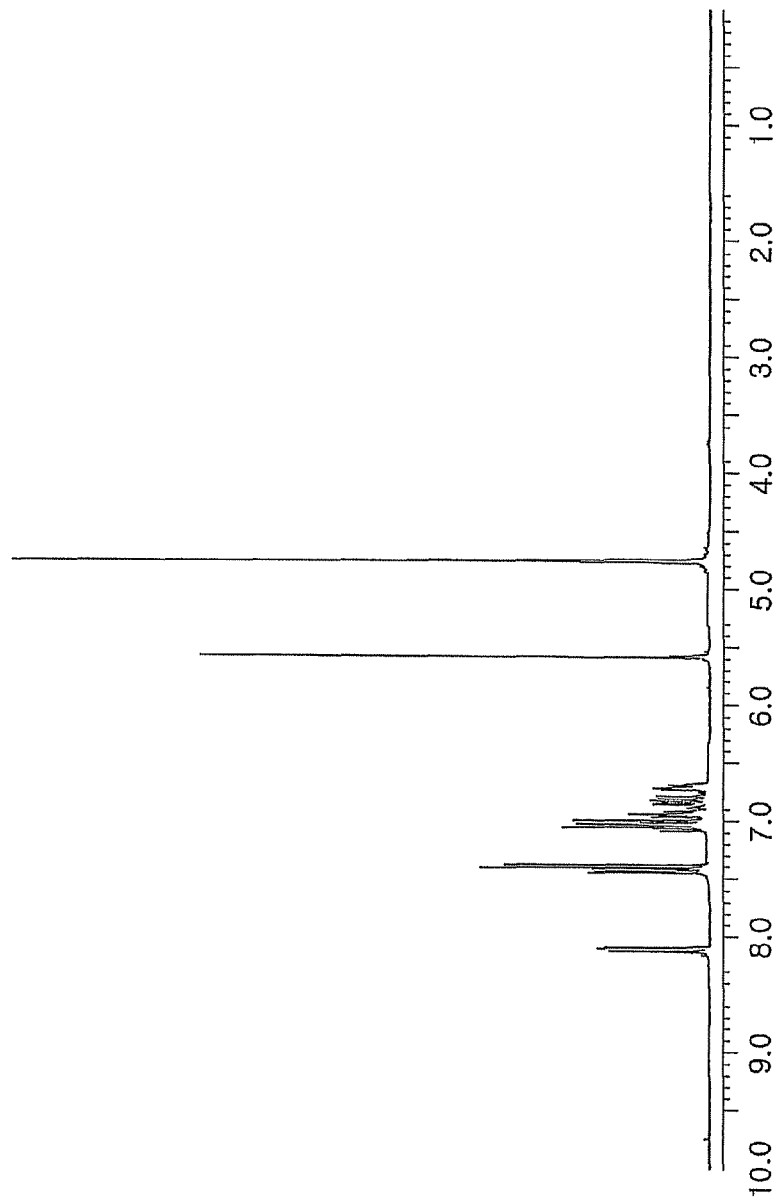

The structure of 8HQ-34DFA of Formula 11 was confirmed by NMR spectroscopy performed using a Varian Unity INOVA600 spectrometer at 600 MHz, and the results are shown in FIG. 6.

SYNTHESIS EXAMPLE 7

Preparation of 8HQD-34DFA of Formula 12

A target material was prepared in the same manner as in Synthesis Example 5, except that an alcohol represented by the following formula was used instead of 2 g of 3-hydroxypyridine (21 mmol).

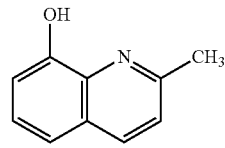

Figure 7:
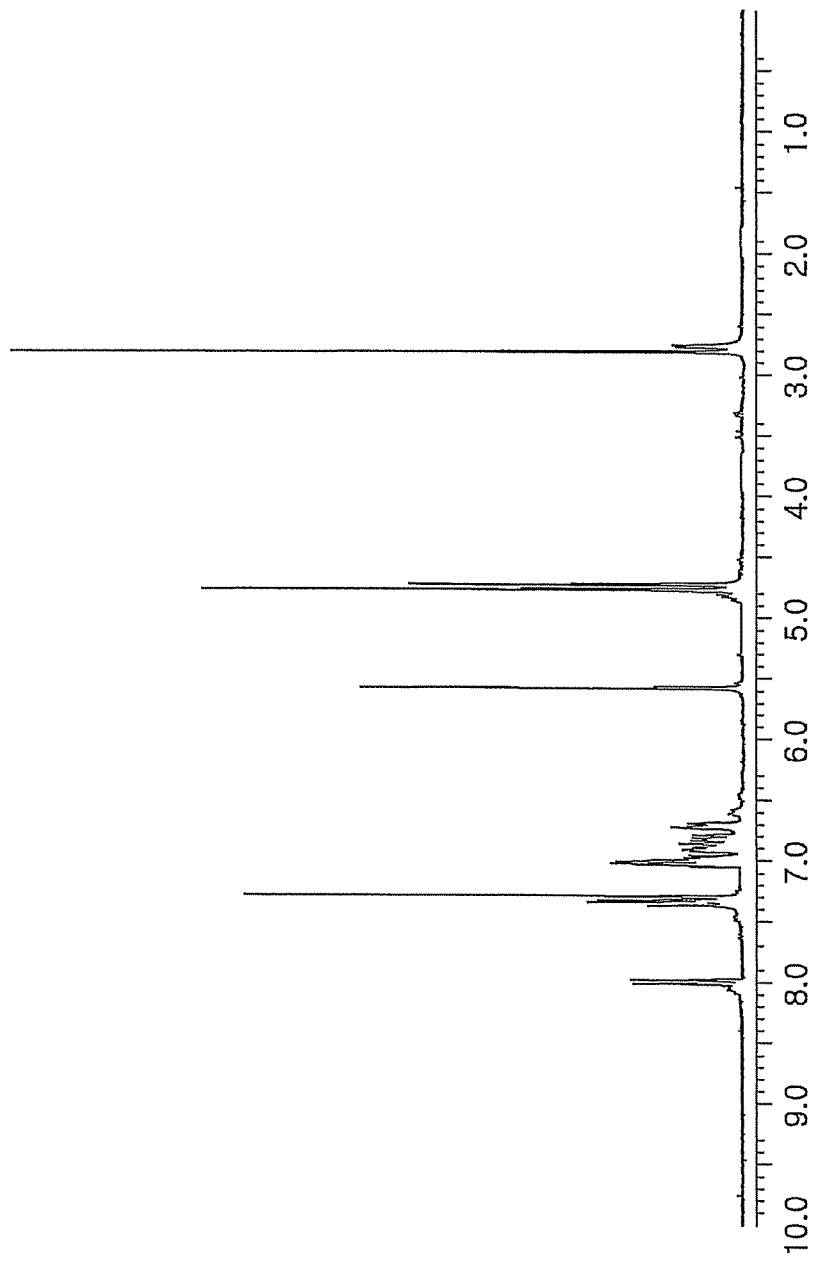

The structure of 8HQD-34DFA of Formula 12 was confirmed by NMR spectroscopy performed using a Varian Unity INOVA600 spectrometer at 600 MHz, and the results are shown in FIG. 7.

SYNTHESIS EXAMPLE 8

Preparation of a Polymer of 4FPh-2AP of Formula 6

20 g of 4FPh-2AP of Formula 6 and dimethylacetamide were mixed together, and then the mixture was cured at about 220° C. to obtain a polymer of 4FPh-2AP of Formula 6.

Figure 8:
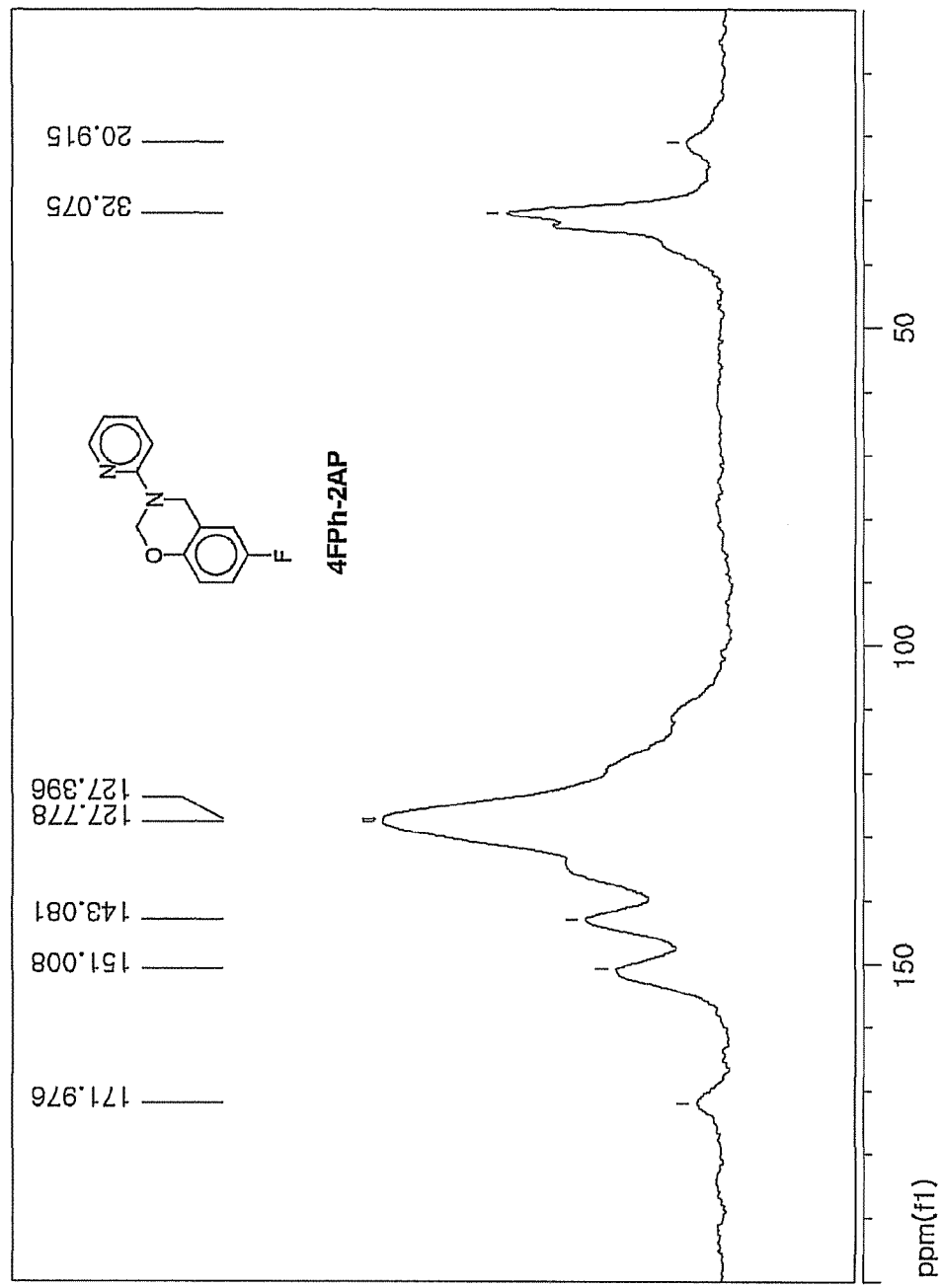
FIG. 8 is a graph showing the NMR spectrum of a polymer of a benzoxazine-based monomer prepared in Synthesis Example 8.

The structure of the solid-phase polymer of 4FPh-2AP of Formula 6 was identified by a solid nuclear magnetic resonance (NMR) spectroscopy performed using a Varian Unity INOVA600 spectrometer at 600 MHz, and the results are shown in FIG. 8.

REFERENCE EXAMPLE 1

Preparation of t-BuPh-a 15 g of t-butylphenol (0.1 mol), 6.31 g of para-formaldehyde (0.21 mol), and 10.24 g of aniline (0.11 mol) were sequentially added in a 100 ml one-neck round bottom flask, and then mixed in an oil bath at 90° C.

The reaction mixture was opaque in an early stage of the reaction, and about 30 minutes after the reaction, the reaction mixture converted into a dark brown material in the form of a transparent gel. The reaction mixture was quenched with tetrahydrofurane (THF) and cooled to room temperature.

The crude product cooled to room temperature was base washed twice by solvent extraction that used an aqueous 1N NaOH solution, and then washed once again with deionized water. After the washing process was terminated, the organic layer was dried using $MgSO_4$, and then continuously filtered. The solvent was removed from the filtered solution using a rotary evaporator, and then the purified product was dried in a vacuum oven at 40° C. for 6 hours to obtain t-BuPh-a.

Figure 9:
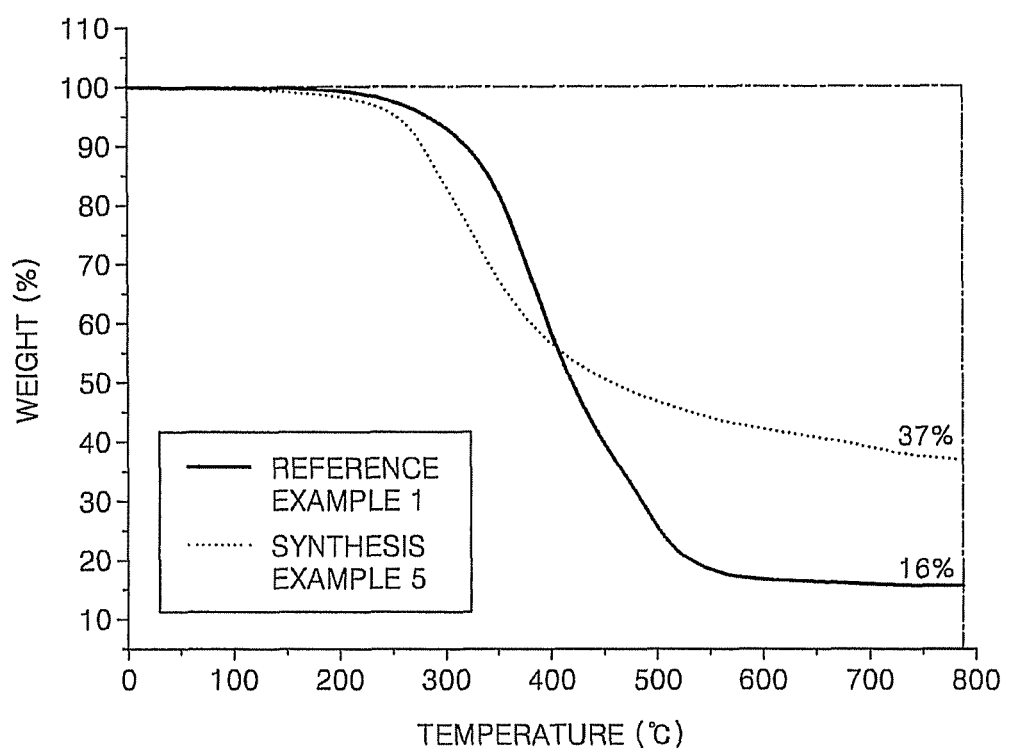
FIG. 9 is a graph showing thermogravimetric analysis (TGA) results of 3HP-34DFA prepared in Synthesis Example 5 and t-BuPh-a prepared in Reference Example 1.

Thermal stabilities of 3HP-34DFA prepared in Synthesis Example 5 and t-BuPh-a prepared in Reference Example 1 were evaluated using thermogravimetric analysis (TGA). The results are shown in FIG. 9. In FIG. 9, thermogravimetric loss was measured at 800° C.

Referring to FIG. 9, it was confirmed that 3HP-34DFA of Synthesis Example 5 had less thermogravimetric loss at a temperature of 800° C. or more than did t-BuPh-a. From the result, it can be seen that 3HP-34DFA of Synthesis Example 5 has excellent thermal stability compared to t-BuPh-a.

EXAMPLE 1

Preparation of Electrode for Fuel Cell and Fuel Cell Including the Electrode 1 g of a catalyst in which 50 wt % of PtCo was supported on carbon and 3 g of NMP were added to a stirrer, and the mixture was stirred using a mortar to prepare a slurry. An NMP solution of 4FPh-2AP of Synthesis Example 1 was added to the slurry so that the resultant contained 0.025 g of 4FPh-2AP of Formula 6. The resultant was further stirred.

Subsequently, an NMP solution of 5 wt % of polyvinylidenefluoride was added to the resultant so that the resultant contained 0.025 g of polyvinylidenefluoride. The resultant was mixed for 10 minutes to prepare a slurry used to form a cathode catalyst layer.

Carbon paper was cut to a size of 4×7 cm², fixed on a glass plate, and coated by a doctor blade (Sheen instrument). The gap interval was adjusted to 600 μm.

The slurry to form a cathode catalyst layer was coated onto the carbon paper, and the resultant was dried at room temperature for 1 hour, dried at 80° C. for 1 hour, dried at 120° C. for 30 minutes, and dried at 150° C. for 15 minutes to prepare a cathode (a fuel electrode). The loading amount of PtCo in the prepared cathode was 2.1 mg/cm².

An electrode prepared by the following processes was used as an anode.

2 g of a catalyst in which 50 wt % of Pt was supported on carbon and 9 g of NMP were added to a stirrer, and the mixture was stirred for 2 minutes using a high speed stirrer.

Subsequently, a solution in which 0.05 g of polyvinylidenefluoride was dissolved in 1 g of NMP was added to the mixture, and the resultant was further stirred for 2 minutes to prepare a slurry used for forming an anode catalyst layer. The slurry used for forming an anode catalyst layer was coated on carbon paper coated with a microporous layer using a bar coater. As a result, preparation of the anode was completed. The loading amount of Pt in the prepared anode was 1.3 mg/cm².

Separately, 60 parts by weight of the benzoxazine-based monomer of Formula 18, 3 parts by weight of the benzoxazine-based monomer of Formula 24 where R₂ was a phenyl group, and 37 parts by weight of polybenzimidazole were blended together, and then the mixture was cured at about 220° C.

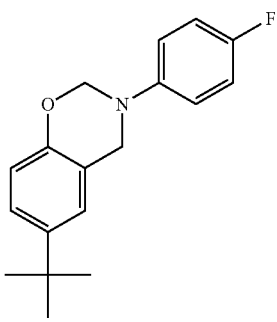 [SMILES: CC(C)(C)c1ccc2c(c1)CN(c1ccc(F)cc1)CO2]

Benzoxazine-based Monomer A

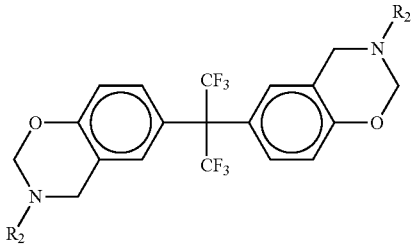

wherein $R_2$ is a phenyl group
Benzoxazine-based Monomer B

Subsequently, the resultant was impregnated with 85 wt % of phosphoric acid at 80° C. for over 4 hours to form an electrolyte membrane. Herein, the amount of phosphoric acid was about 480 parts by weight based on 100 parts by weight of the total weight of the electrolyte membrane.

The electrolyte membrane was disposed between the cathode and the anode to prepare a MEA. Herein, the cathode and anode were not impregnated with phosphoric acid.

To prevent gas permeation between the cathode and the anode, a TEFLON membrane for a main gasket with a thickness of 200 μm and a TEFLON membrane for a subgasket with a thickness of 20 μm were joined and disposed between the electrode and the electrolyte membrane.

Electricity was generated by causing hydrogen to flow into the anode (flowrate: 100 cc/m) and causing air to flow into the cathode (flowrate: 250 cc/m) at 150° C. under a condition where the electrolyte membrane was not humidified, and properties of a fuel cell prepared were measured. Herein, an electrolyte doped with a phosphoric acid was used, and thus the performance of the fuel cell improved as time elapsed. Thus, aging was performed until an operating voltage reached a peak, and then the properties of the fuel cell were finally evaluated. In addition, the area of the cathode and anode was fixed to a size of 2.8×2.8 (7.84 cm²), and the thickness of the cathode was about 430 μm and the thickness of the anode was about 390 μm.

EXAMPLE 2-6

Preparation of Electrode for Fuel Cell and Fuel Cell Including the Electrode

Cathodes were prepared in the same manner as in Example 1, except that 4FPh-3AP of Synthesis Example 2, 34DFph2APMD of Synthesis Example 3, 34DFph4AP of Synthesis Example 4, 3HP-34DFA of Synthesis Example 5, and 8HQ-34DFA of Synthesis Example 6, respectively were used instead of 4FPh-2AP of Synthesis Example 1, and fuel cells using the cathodes were manufactured.

COMPARATIVE EXAMPLE 1

Preparation of Electrode for Fuel Cell and Fuel Cell Including the Electrode

A cathode was prepared in the same manner as in Example 1, except that 4FPh2AP of Formula 2 of Synthesis Example 1 was not used, and a fuel cell using the cathode was manufactured.

Figure 10:
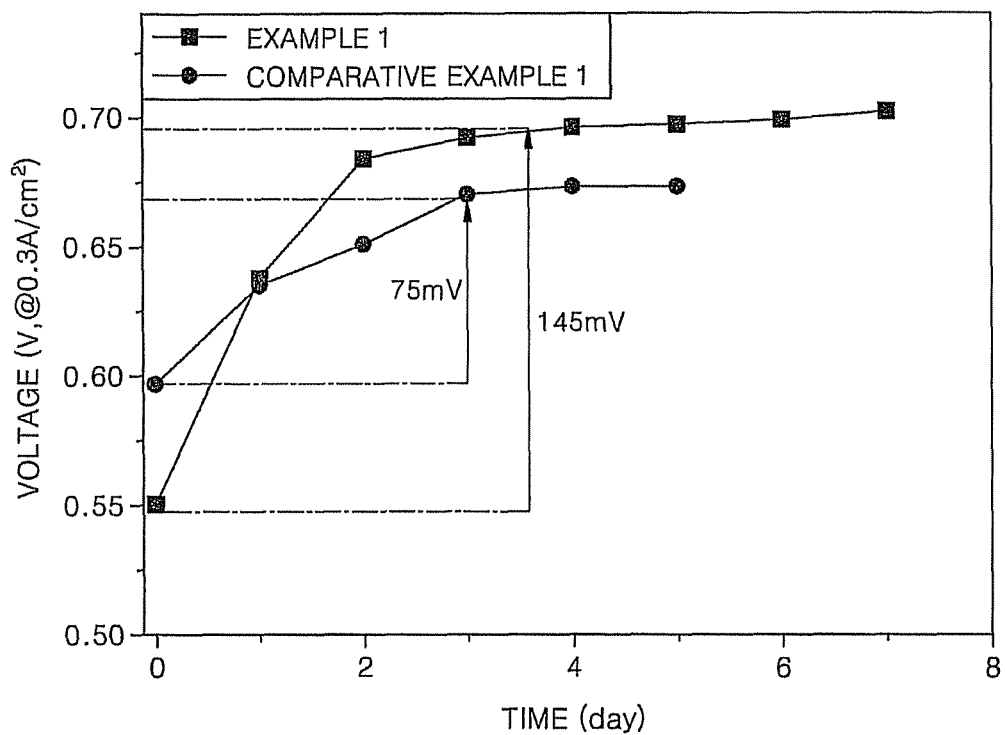
FIG. 10 is a graph showing a change in voltage according to time of fuel cells manufactured in Example 1 and Comparative Example 1.

FIG. 10 is a graph showing a change in voltage with respect to time of fuel cells manufactured in Example 1 and Comparative Example 1.

Referring to FIG. 10, although the fuel cell of Example 1 had low initial performance, it had improved voltage performance by fast activation compared to the fuel cell of Comparative Example 1.

Figure 11:
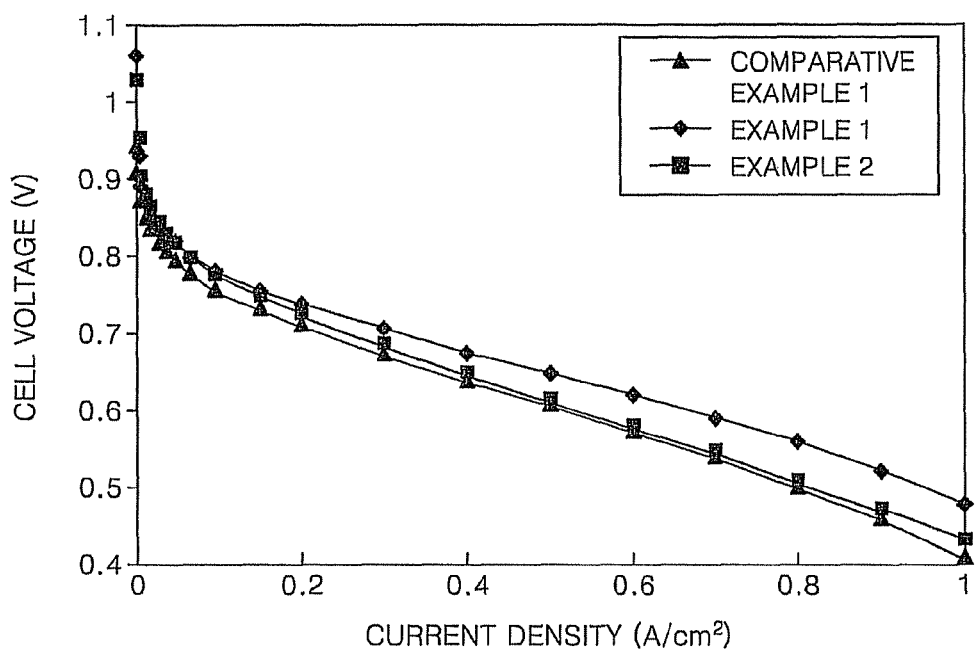
FIG. 11 is a graph showing a change in cell voltage according to current density of fuel cells manufactured in Examples 1 and 2 and Comparative Example 1.

In addition, a change in cell potential with respect to current density of the fuel cells of Examples 1 and 2 and Comparative Example 1 was measured, and the results are shown in FIG. 11. FIG. 11 is a graph showing a change in cell voltage with respect to current density of the fuel cells manufactured in Examples 1 and 2 and Comparative Example 1.

Referring to FIG. 11, the fuel cells of Examples 1 and 2 had improved cell voltage characteristics with respect to current density compared to the fuel cell of Comparative Example 1.

EXAMPLE 7

Preparation of Electrolyte Membrane for Fuel Cell and Fuel Cell Using the Electrolyte Membrane 1 g of a catalyst in which 50 wt % of PtCo was supported on carbon and 3 g of NMP as a solvent were added to a stirrer, and the mixture was stirred using a mortar to prepare a slurry. An NMP solution of 4FPh-2AP of Formula 6 of Synthesis Example 1 was added to the slurry in order that the resultant contained 0.025 g of 4FPh-2AP of Formula 6. The resultant was further stirred.

Subsequently, a NMP solution of 5 wt % of polyvinylidenefluoride was added to the resultant to make the resultant contain 0.025 g of polyvinylidenefluoride. The resultant was mixed for 10 minutes to prepare a slurry used for forming a cathode catalyst layer.

Carbon paper was cut to a size of 4×7 cm², fixed on a glass plate, and coated by a doctor blade (Sheen instrument). Herein, a gap interval was adjusted to 600 μm.

The slurry used for forming a cathode catalyst layer was coated on the carbon paper, and the resultant was dried at room temperature for 1 hour, dried at 80° C. for 1 hour, dried at 120° C. for 30 minutes, and dried at 150° C. for 15 minutes to prepare a cathode (a fuel electrode). The loading amount of PtCo in the prepared cathode was 2.32 mg/cm².

An electrode prepared by the following processes was used as an anode.

2 g of a catalyst in which 50 wt % of Pt was supported on carbon and 9 g of NMP as a solvent were added to a stirrer, and the mixture was stirred for 2 minutes using a high speed stirrer.

Subsequently, a solution in which 0.05 g of polyvinylidenefluoride was dissolved in 1 g of NMP was added to the mixture, and the resultant was further stirred for 2 minutes to prepare a slurry used for forming an anode catalyst layer. The slurry used for forming an anode catalyst layer was coated on carbon paper coated with a microporous layer using a bar coater. As a result, preparation of the anode was completed. The loading amount of Pt in the prepared anode was 1.44 mg/cm².

Separately, 65 parts by weight of 4FPh-2AP of Formula 6 of Synthesis Example 1, and 35 parts by weight of polybenzimidazole (PBI) represented by the following formula were blended together, and then the mixture was cured at about 220° C.

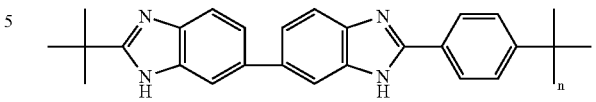

A weight average molecular weight of polybenzimidazole was about 20,000.

Subsequently, the resultant was impregnated with 85 wt % of phosphoric acid at 80° C. for over 4 hours to form an electrolyte membrane. Herein, the amount of phosphoric acid was about 500 parts by weight based on 100 parts by weight of the total weight of the electrolyte membrane.

The electrolyte membrane was disposed between the cathode and the anode to prepare an MEA. Herein, the cathode and anode were not impregnated with phosphoric acid.

To prevent gas permeation between the cathode and the anode, a TEFLON membrane for a main gasket with a thickness of 200 μm and a TEFLON membrane for a subgasket with a thickness of 20 μm were joined and disposed between the electrode and the electrolyte membrane. The pressure applied to the MEA was adjusted to 1, 2, 3 N-m Torque step by step using a wrench to assemble a cell.

Electricity was generated by causing hydrogen to flow into the anode (flowrate: 100 cc/m) and causing air to flow into the cathode (flowrate: 250 cc/m) at 150° C. under a condition where the electrolyte membrane was not humidified, and properties of a fuel cell prepared were measured. Herein, an electrolyte doped with a phosphoric acid was used, and thus the performance of the fuel cell improved as time elapsed. Thus, aging was performed until an operating voltage reached a peak, and then the properties of the fuel cell were finally evaluated. In addition, the area of the cathode and anode was fixed to a size of 2.8×2.8 (7.84 cm²), and the thickness of the cathode was about 430 μm and the thickness of the anode was about 390 μm.

Figure 12:
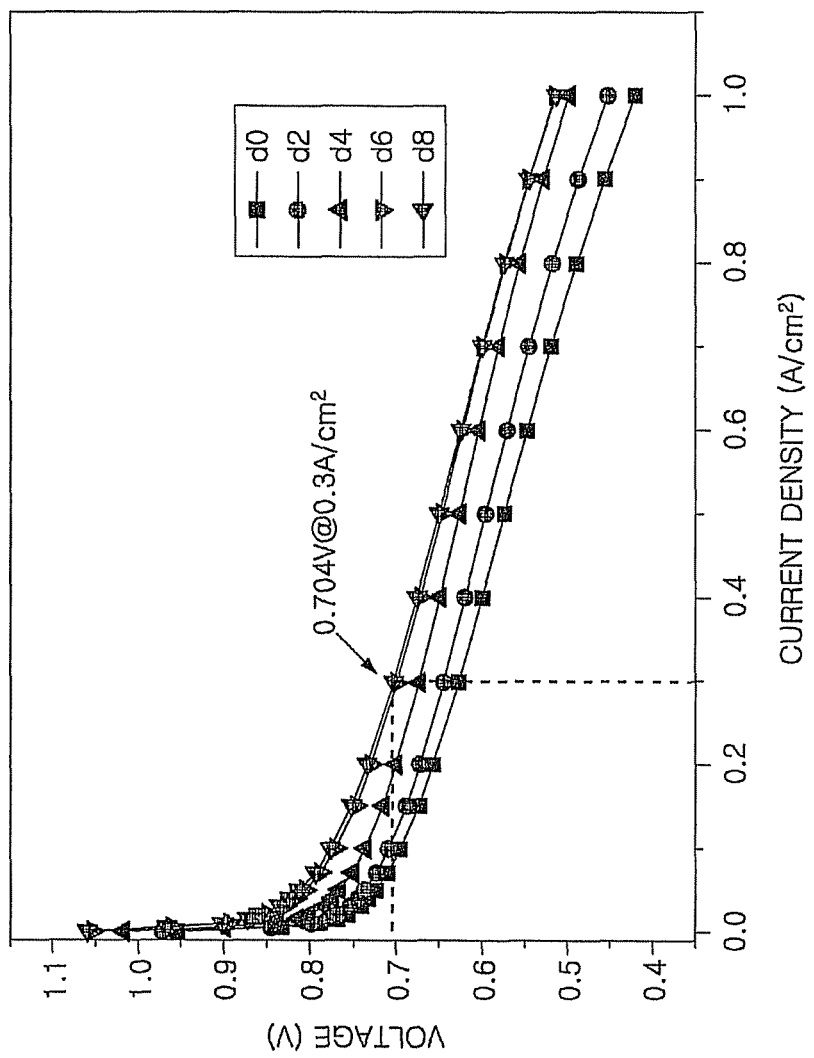
FIG. 12 is a graph showing cell voltage according to current density and according to days of operation of a fuel cell manufactured in Example 7.

Cell voltage according to current density of the fuel cell manufactured in Example 7 was measured, and the results are shown in FIG. 12. FIG. 12 is a graph showing results of cell voltage according to current density of the fuel cell of Example 7 after d0, d2, d4, d6, and d8, wherein d0 denotes right after operation, d2 denotes after 2 days, d4 denotes after 4 days, d6 denotes after 6 days, and d8 denotes after 8 days.

Referring to FIG. 12, the fuel cell of Example 7 have increased cell voltage according to operating time.

Figure 13:
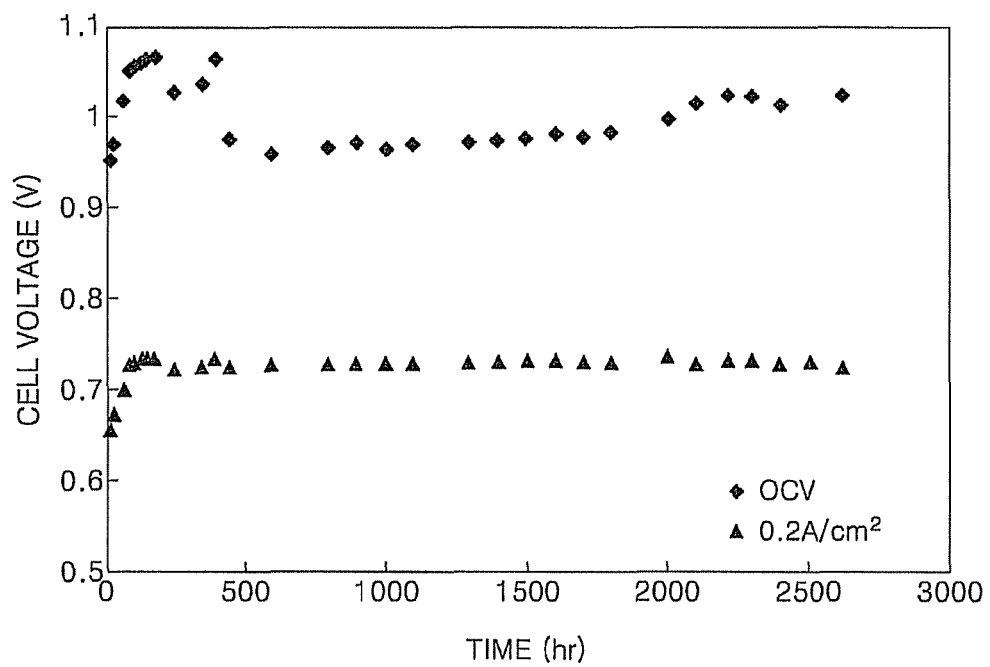
FIG. 13 is a graph showing evaluation results of durability of an electrolyte membrane prepared in Example 7.

Durability of the electrolyte membrane prepared in Example 7 was measured, and the results are shown in FIG. 13. In FIG. 13, "OCV" denotes an open circuit voltage, and "0.2 A/cm²" denotes cell voltage at a current density of 0.2 A/cm².

Referring to FIG. 13, electrolyte membrane prepared in Example 7 shows nearly no voltage drop until 2500 hours.

EXAMPLE 8

Preparation of Electrolyte Membrane for Fuel Cell and Fuel Cell Using the Electrolyte Membrane An electrolyte membrane and a fuel cell using the electrolyte membrane were prepared in the same manner as in Example 7, except that 3HP-34DFA represented by Formula 10 was used instead of 4FPh-2AP of Formula 6 in the formation of the electrolyte membrane.

Figure 14:
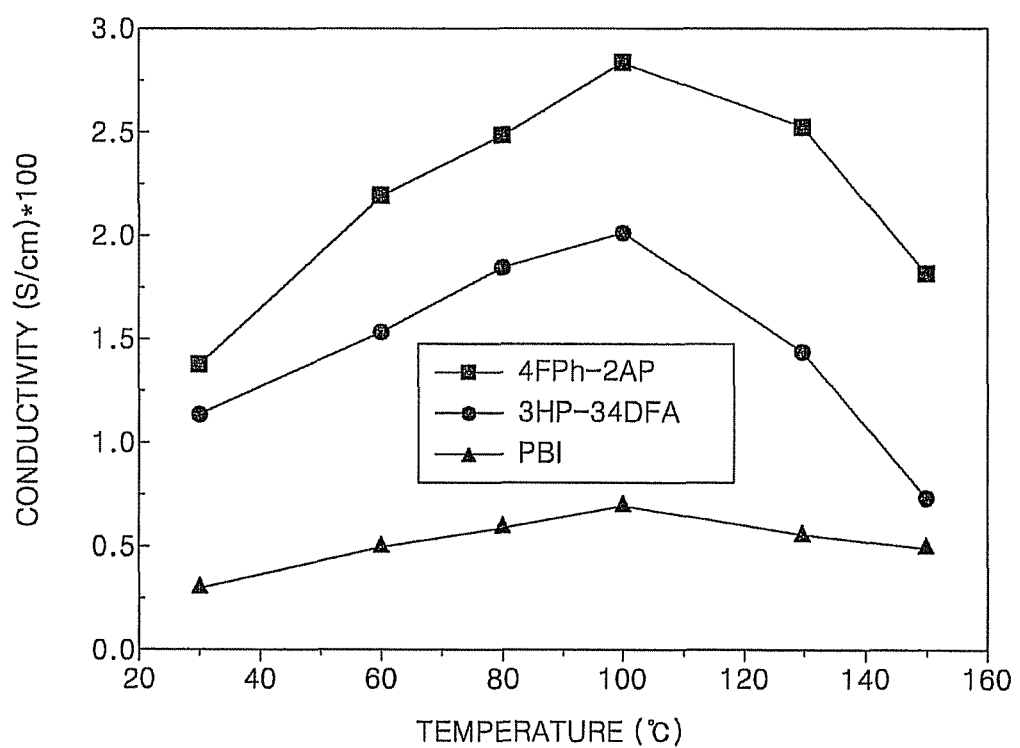
FIGS. 14 and 15 are graphs showing measurement results of conductivity according to temperature and phosphoric acid doping level of electrolyte membrane prepared in Examples 7 and 8.
Figure 15:
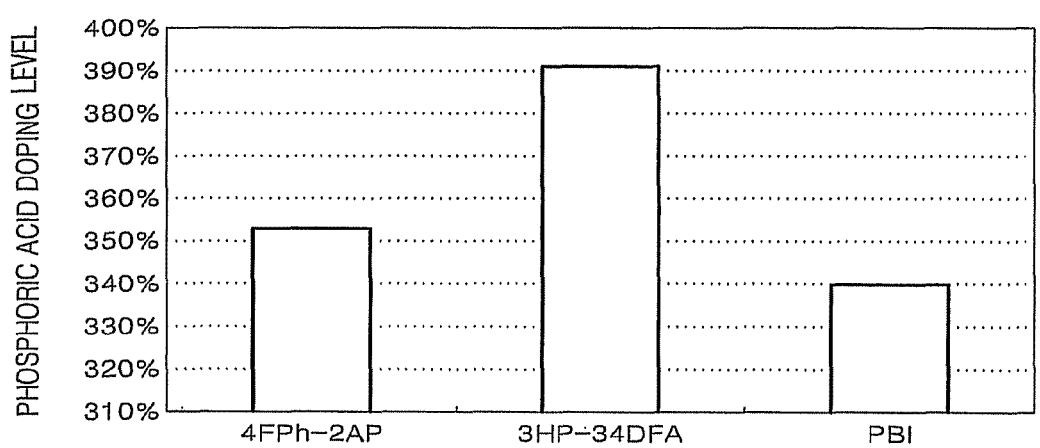

Conductivity according to temperature and phosphoric acid doping level of the electrolyte membranes prepared in Examples 7 and 8 were measured, and the results are respectively shown in FIGS. 14 and 15.

Referring to FIGS. 14 and 15, the electrolyte membranes of Examples 7 and 8 have higher ionic conductivity and excellent durability.

Referring to FIG. 15, the electrolyte membranes of Examples 7 and 8 have higher conductivity compared with the PBI electrolyte membrane.

In FIG. 15, the phosphoric acid doping level of 4FPh-2AP is 352%. This represents that the doping level is 352 parts by weight of phosphoric acid based on 100 parts by weight of 4FPh-2AP.

Figure 16:
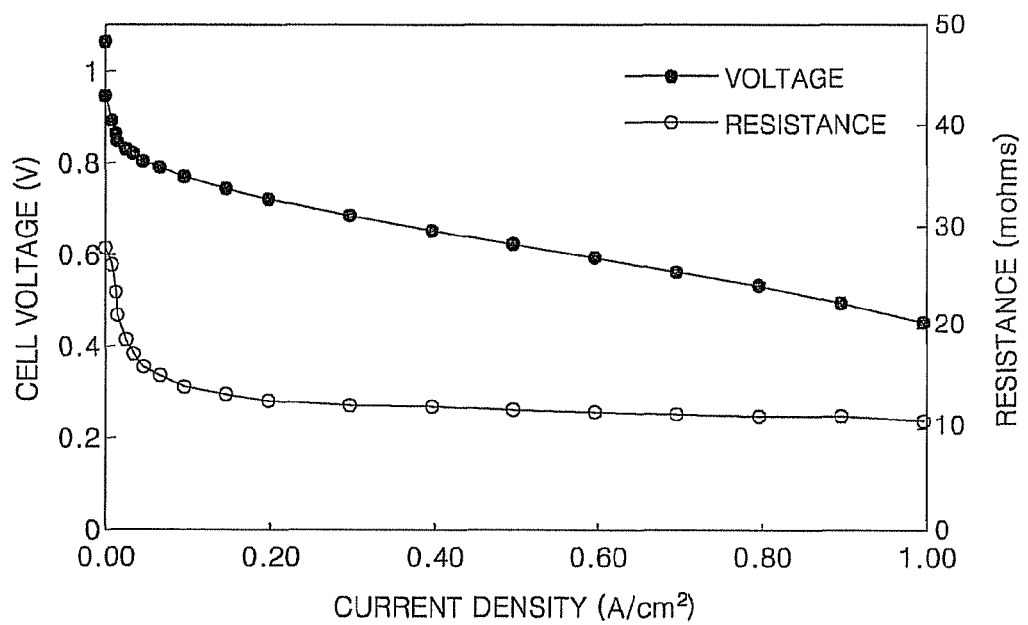
FIG. 16 is a graph showing a change in cell voltage and resistance according to current density of an electrolyte membrane prepared in Example 8.

In addition, a change in voltage and resistance according to current density of the fuel cell manufactured in Example 8 was measured, and the results are shown in FIG. 16. Referring to FIG. 16, the fuel cell of Example 8 has excellent voltage and resistance characteristics.

EXAMPLE 9

Preparation of Electrolyte Membrane for Fuel Cell and Fuel Cell Using the Electrolyte Membrane An electrolyte membrane and a fuel cell using the electrolyte membrane were prepared in the same manner as in Example 7, except that 3HQ-34DFA represented by Formula 11 was used instead of 4FPh-2AP of Formula 6 in the formation of the electrolyte membrane.

Figure 17:
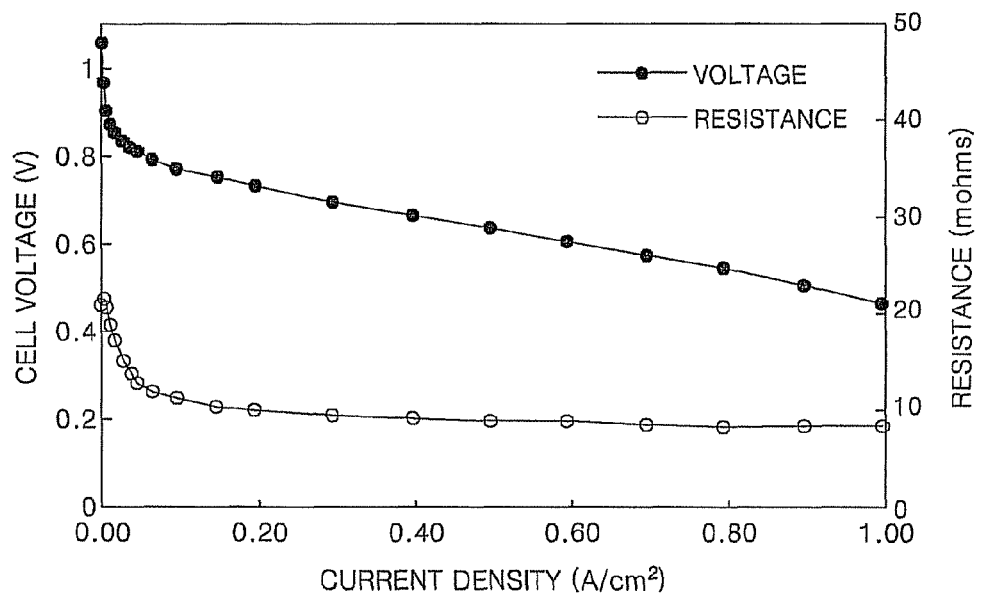
FIG. 17 is a graph showing a change in cell voltage and resistance according to current density of an electrolyte membrane prepared in Example 9.

A change in cell voltage and resistance according to current density of the fuel cell of Example 9 was measured, and the results are shown in FIG. 17.

Referring to FIG. 17, the fuel cell manufactured in Example 9 has excellent cell voltage and resistance characteristics.

EXAMPLE 10

Preparation of Electrolyte Membrane for Fuel Cell and Fuel Cell Using the Electrolyte Membrane An electrolyte membrane and a fuel cell using the electrolyte membrane were prepared in the same manner as in Example 7, except that 3HQD-34DFA represented by Formula 12 was used instead of 4FPh-2AP of Formula 6 in the formation of the electrolyte membrane.

Figure 18:
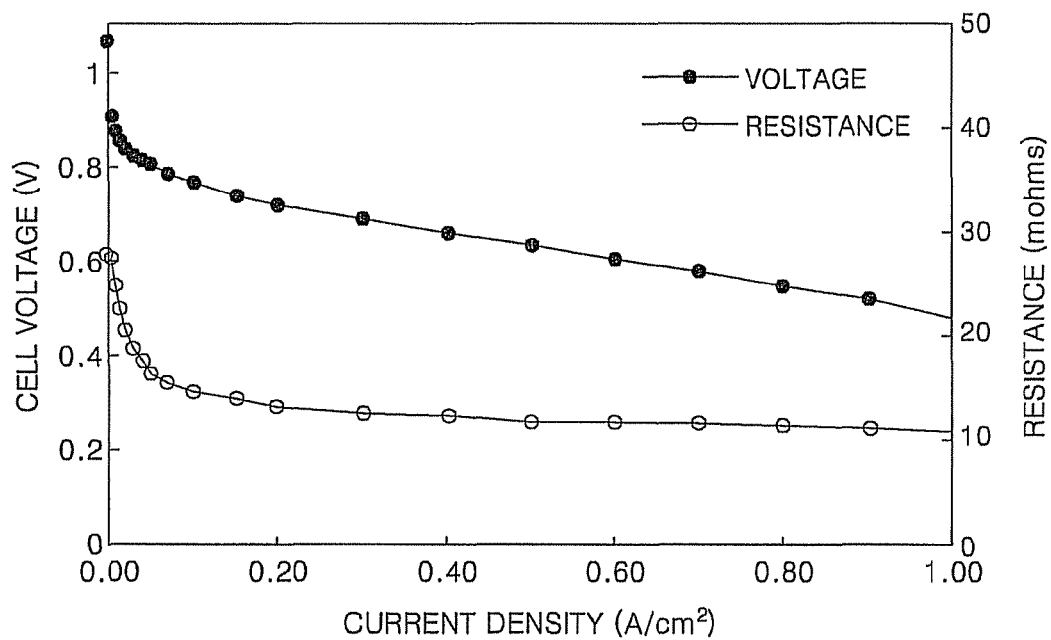
FIG. 18 is a graph showing a change in cell voltage and resistance according to current density of an electrolyte membrane prepared in Example 10.

A change in cell voltage and resistance according to current density of the fuel cell of Example 10 was measured, and the results are shown in FIG. 18.

Referring to FIG. 18, the fuel cell manufactured in Example 10 has excellent cell voltage and resistance characteristics as in the fuel cell of Example 7.

Figure 19:
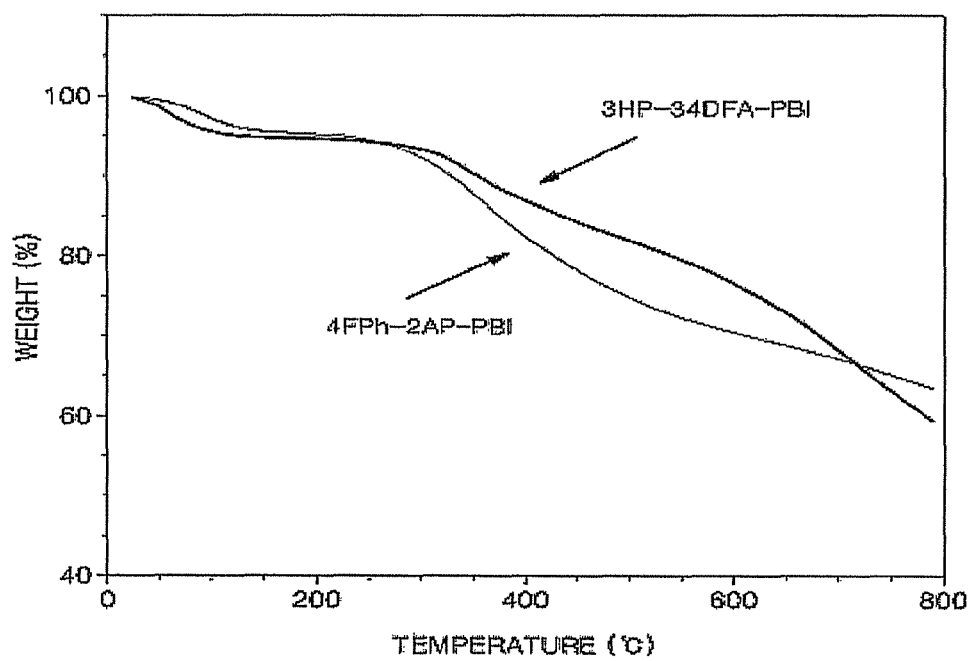
FIG. 19 is a graph showing evaluation results of thermal stability of electrolyte membrane prepared in Examples 7 and 8.

Thermal stabilities of the electrolyte membranes prepared in Examples 7 and 8 were evaluated using thermogravimetric analysis (TGA). The results are shown in FIG. 19. In FIG. 19, thermogravimetric loss was measured at 800° C.

Referring to FIG. 19, the electrolyte membranes of Examples 7 and 8 have excellent thermal stability.

EXAMPLE 11

Preparation of Fuel Cell 1 g of a catalyst in which 50 wt % of PtCo was supported on carbon and 3 g of NMP as a solvent were added to a stirrer, and the mixture was stirred using a mortar to prepare a slurry. A NMP solution of 4FPh-2AP of Formula 6 was added to the slurry in order that the resultant contained 0.025 g of 4FPh-2AP of Formula 6. The resultant was further stirred.

Subsequently, a NMP solution of 5 wt % of polyvinylidenefluoride was added to the resultant to make the resultant contain 0.025 g of polyvinylidenefluoride. The resultant was mixed for 10 minutes to prepare a slurry used for forming a cathode catalyst layer.

Carbon paper was cut to a size of 4×7 $cm^2$, fixed on a glass plate, and coated by a doctor blade (Sheen instrument). Herein, a gap interval was adjusted to 600 μm.

The slurry used for forming a cathode catalyst layer was coated on the carbon paper, and the resultant was dried at room temperature for 1 hour, dried at 80° C. for 1 hour, dried at 120° C. for 30 minutes, and dried at 150° C. for 15 minutes to prepare a cathode (a fuel electrode). The loading amount of PtCo in the prepared cathode was 2.03 $mg/cm^2$.

An electrode prepared by the following processes was used as an anode. 2 g of a catalyst in which 50 wt % of Pt was supported on carbon and 9 g of NMP as a solvent were added to a stirrer, and the mixture was stirred for 2 minutes using a high speed stirrer.

Subsequently, a solution in which 0.05 g of polyvinylidenefluoride was dissolved in 1 g of NMP was added to the mixture, and the resultant was further stirred for 2 minutes to prepare a slurry for forming an anode catalyst layer. The slurry for forming an anode catalyst layer was coated onto carbon paper coated with a microporous layer using a bar coater. As a result, preparation of the anode was completed. The loading amount of Pt in the prepared anode was 1.34 $mg/cm^2$.

Separately, 65 parts by weight of 4FPh-2AP of Formula 6 and 35 parts by weight of polybenzimidazole were blended together, and then the mixture was cured at about 220° C.

Then, the resultant was impregnated with 85% by weight of phosphoric acid at 80° C. for longer than 4 hours to prepare an electrolyte membrane. The amount of phosphoric acid was about 440 parts by weight based on 100 parts by weight of electrolyte membrane.

A membrane electrode assembly (MEA) was prepared by interposing the electrolyte membrane between the cathode and the anode. The cathode and anode were not impregnated with phosphoric acid.

A 200 μm TEFLON membrane for a main gasket and a 20 μm TEFLON membrane for a sub gasket were overlapped on an interface between the electrodes and electrolyte membrane in order to prevent gas permeation between the cathode and the anode. The pressure applied to the MEA was adjusted to 1, 2, 3 N-m torque step by step using a wrench to assemble a cell.

Characteristics of fuel cells were measured while operating at 150° C. by supplying hydrogen to the anode at 100 cc/m and supplying air to the cathode at 250 cc/m while the electrolyte membrane was not hydrated. Since cell efficiency increases with time when an electrolyte doped with phosphoric acid is used, the final efficiency was measured after the fuel cell had been aged until the operational voltage was maximized. The area of the cathode and the anode was fixed to 2.8×2.8=7.84 $cm^2$, and the thickness of the cathode was about 430 μm and the thickness of the anode was about 390 μm, although the thicknesses of the cathode and the anode may have varied according to the distribution of the carbon paper.

COMPARATIVE EXAMPLE 2

Preparation of Fuel Cell

A fuel cell was prepared in the same manner as in Example 11, except that a polybenzimidazole (PBI) membrane was used as an electrolyte membrane and 4FPh2AP of Formula 6 was not used in the preparation of the cathode.

Figure 20:
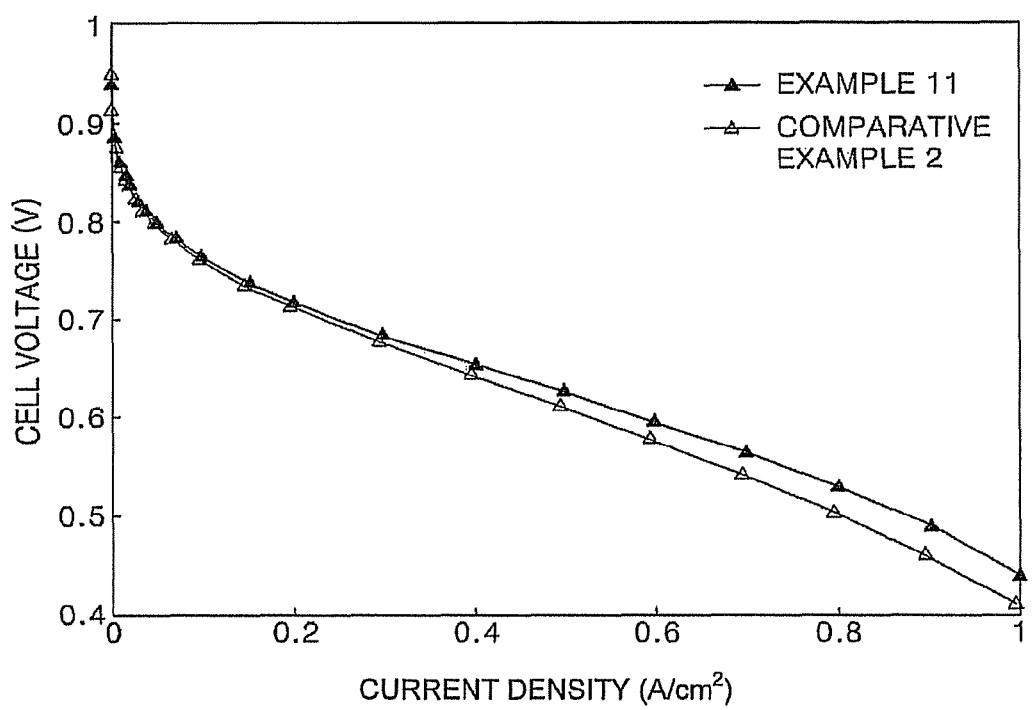
FIG. 20 is a graph showing cell voltage according to current density of fuel cells manufactured in Example 11 and Comparative Example 2.

Cell voltage characteristics with respect to current density of the fuel cells prepared in Example 11 and Comparative Example 2 were measured, and the results are shown in FIG. 20.

Referring to FIG. 20, cell voltage of the fuel cell of Example 11 was improved compared with that of the fuel cell of Comparative Example 2.

While aspects of the present invention have been particularly shown and described with reference to differing embodiments thereof, it should be understood that these exemplary embodiments should be considered in a descriptive sense only and not for purposes of limitation. Descriptions of features or aspects within each embodiment should typically be considered as available for other similar features or aspects in the remaining embodiments.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A benzoxazine-based monomer represented by Formula 1 below:

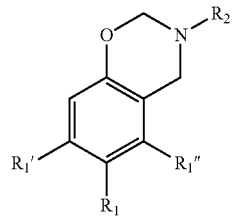

<Formula 1> wherein at least one of $R_1$, $R_1'$, and $R_1''$ is a halogen atom, a halogenated $C_1$-$C_{20}$ alkyl group, a halogenated $C_1$-$C_{20}$ alkoxy group, a halogenated $C_2$-$C_{20}$ alkenyl group, a halogenated $C_2$-$C_{20}$ alkynyl group, a halogenated $C_6$-$C_{20}$ aryl group, a halogenated $C_6$-$C_{20}$ aryloxy group, a halogenated $C_2$-$C_{20}$ heteroaryl group, a halogenated $C_2$-$C_{20}$ heteroaryloxy group, a halogenated $C_4$-$C_{20}$ cycloalkyl group, or a halogenated $C_2$-$C_{20}$ heterocyclic group, $R_2$ is a substituted or unsubstituted nitrogen-containing $C_2$-$C_{20}$ heterocyclic group, and any remaining ones of $R_1$, $R_1'$, and $R_1''$ are hydrogen.

2. The benzoxazine-based monomer of claim 1, wherein, in Formula 1, the at least one of $R_1$, $R_1'$, and $R_1''$ is fluorine, a fluorinated $C_1$-$C_{20}$ alkyl group, a fluorinated $C_6$-$C_{20}$ aryl group, a fluorinated $C_2$-$C_{20}$ heteroaryl group, a fluorinated $C_2$-$C_{20}$ heteroaryloxy group, a fluorinated $C_4$-$C_{20}$ cycloalkyl group, or a fluorinated $C_2$-$C_{20}$ heterocyclic group, and $R_2$ is a nitrogen-containing $C_3$-$C_6$ heterocyclic group.

3. The benzoxazine-based monomer of claim 2, wherein the nitrogen-containing $C_3$-$C_6$ heterocyclic group is one selected from the groups represented by the following formulae.

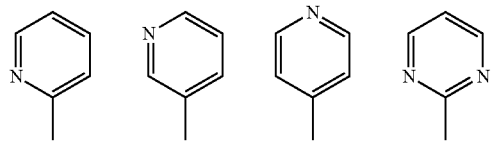

4. The benzoxazine-based monomer of claim 2, wherein the fluorinated $C_6$-$C_{20}$ aryl group is one selected from the groups represented by the following formulae.

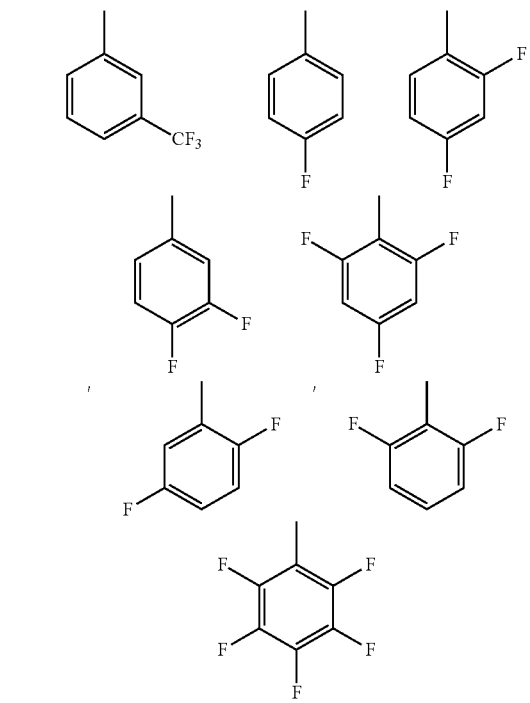

5. The benzoxazine-based monomer of claim 1, wherein, in Formula 1, the at least one of $R_1$, $R_1'$, and $R_1''$ is fluorine, a fluorinated $C_1$-$C_{20}$ alkyl group, a fluorinated $C_6$-$C_{20}$ aryl group, a fluorinated $C_2$-$C_{20}$ heteroaryl group, a fluorinated $C_2$-$C_{20}$ heteroaryloxy group, a fluorinated $C_4$-$C_{20}$ cycloalkyl group, or a fluorinated $C_2$-$C_{20}$ heterocyclic group, and $R_2$ is a nitrogen-containing $C_3$-$C_6$ heterocyclic group.

6. The benzoxazine-based monomer of claim 1, which is one selected from the compounds represented by Formulae 6 through 9 below.

<Formula 6>

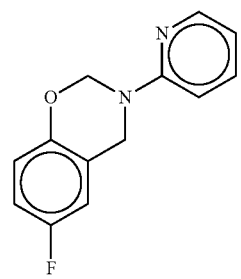

-continued

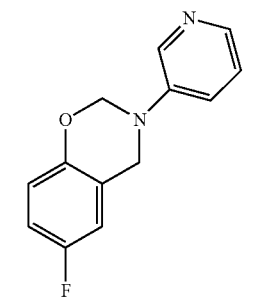
<Formula 7>

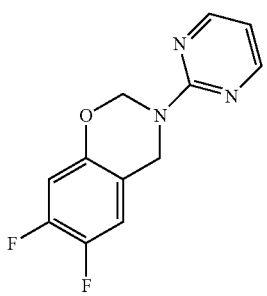
<Formula 8>

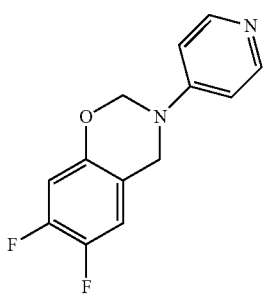
<Formula 9>

7. A benzoxazine-based monomer represented by Formula 1 below:

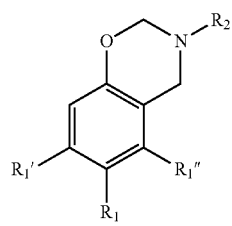
<Formula 1> wherein at least one of $R_1$, $R_1'$, and $R_1''$ is a halogen atom, a halogenated $C_1$-$C_{20}$ alkyl group, a halogenated $C_1$-$C_{20}$ alkoxy group, a halogenated $C_2$-$C_{20}$ alkenyl group, a halogenated $C_2$-$C_{20}$ alkynyl group, a halogenated $C_6$-$C_{20}$ aryl group, a halogenated $C_6$-$C_{20}$ aryloxy group, a halogenated $C_2$-$C_{20}$ heteroaryl group, a halogenated $C_2$-$C_{20}$ heteroaryloxy group, a halogenated $C_4$-$C_{20}$ cycloalkyl group, or a halogenated $C_2$-$C_{20}$ heterocyclic group and any remaining ones of $R_1$, $R_1'$, and $R_1''$ are hydrogen, and $R_2$ is a substituted or unsubstituted nitrogen-containing non-halogenated $C_2$-$C_{20}$ heterocyclic group.

8. A monomer that is selected from the compounds represented by Formulae 2 through 5 below:

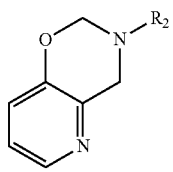
<Formula 2>

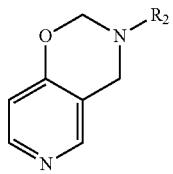
<Formula 3>

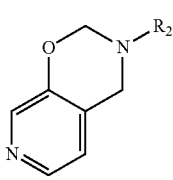
<Formula 4>

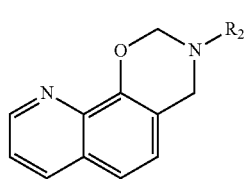
<Formula 5> wherein $R_2$ is a halogen atom, a halogenated $C_1$-$C_{20}$ alkyl group, a halogenated $C_1$-$C_{20}$ alkoxy group, a halogenated $C_2$-$C_{20}$ alkenyl group, a halogenated $C_2$-$C_{20}$ alkynyl group, a halogenated $C_6$-$C_{20}$ aryl group, a halogenated $C_6$-$C_{20}$ aryloxy group, a halogenated $C_2$-$C_{20}$ heteroaryl group, a halogenated $C_2$-$C_{20}$ heteroaryloxy group, a halogenated $C_4$-$C_{20}$ cycloalkyl group, or a halogenated $C_2$-$C_{20}$ heterocyclic group.

9. A polymer which is a polymerization product of the benzoxazine-based monomer according to claim 1 or a polymerization product of the benzoxazine-based monomer according to claim 1 and a crosslinkable compound.

10. A polymer which is a polymerization product of the benzoxazine-based monomer according to claim 2 or a polymerization product of the benzoxazine-based monomer according to claim 2 and a crosslinkable compound.

11. A polymer which is a polymerization product of the benzoxazine-based monomer according to claim 3 or a polymerization product of the benzoxazine-based monomer according to claim 3 and a crosslinkable compound.

12. A polymer which is a polymerization product of the benzoxazine-based monomer according to claim 4 or a polymerization product of the benzoxazine-based monomer according to claim 4 and a crosslinkable compound.

13. A polymer which is a polymerization product of the benzoxazine-based monomer according to claim 5 or a polymerization product of the benzoxazine-based monomer according to claim 5 and a crosslinkable compound.

14. A polymer which is a polymerization product of the benzoxazine-based monomer according to claim 6 or a polymerization product of the benzoxazine-based monomer according to claim 6 and a crosslinkable compound.

15. The polymer of claim 9, wherein the crosslinkable compound is at least one compound selected from the group consisting of polybenzimidazole (PBI), a polybenzimidazole-base complex, polybenzthiazole, polybenzoxazole, and polyimide.

16. The polymer of claim 9, wherein an amount of the crosslinkable compound is in the range of 5-95 parts by weight based on 100 parts by weight of the benzoxazine-based of Formula 1.

17. An electrode for a fuel cell comprising a catalyst layer comprising the polymer of claim 9.

18. The electrode of claim 17, wherein the catalyst layer comprises a catalyst.

19. The electrode of claim 17, wherein the catalyst layer comprises a catalyst, and the amount of the polymer is in the range of 0.001 to 0.65 parts by weight based on 1 part by weight of the catalyst.

20. The electrode of claim 18, wherein the catalyst is:
Pt;
a metal-Pt alloy including Pt and at least one metal selected from the group consisting of Au, Pd, Rh, Ir, Ru, Sn, Mo, Co, and Cr; or
a mixture including Pt and at least one metal selected from the group consisting of Au, Pd, Rh, Ir, Ru, Sn, Mo, Co, and Cr.

21. The electrode of claim 18, wherein the catalyst is a catalyst metal or a support catalyst in which the catalyst metal is loaded on a carbonaceous support,
wherein the catalyst metal is:
Pt;
a metal-Pt alloy including Pt and at least one metal selected from the group consisting of Au, Pd, Rh, Ir, Ru, Sn, Mo, Co, and Cr; or
a mixture including Pt and at least one metal selected from the group consisting of Au, Pd, Rh, Ir, Ru, Sn, Mo, Co, and Cr.

22. The electrode of claim 17, wherein the catalyst layer further comprises at least one proton conductor selected from the group consisting of a phosphoric acid and a $C_1$-$C_{20}$ organic phosphonic acid.

23. The electrode of claim 17, further comprising at least one binder selected from the group consisting of poly(vinylidene fluoride), polytetrafluoroethylene (PTFE), a tetrafluoroethylene-hexafluoropropylene copolymer, fluorinated ethylene propylene (FEP), styrene butadiene rubber (SBR), and polyurethane.

24. The electrode of claim 17, wherein the catalyst layer further comprises a catalyst and a binder,
wherein the binder is at least one selected from the group consisting of poly(vinylidene fluoride), polytetrafluoroethylene (PTFE), a tetrafluoroethylene-hexafluoropropylene copolymer, fluorinated ethylene propylene (FEP), styrene butadiene rubber (SBR), and polyurethane, and
the amount of the binder is in the range of 0.1 to 50 parts by weight based on 100 parts by weight of the catalyst.

25. A fuel cell comprising: a cathode; an anode; and an electrolyte membrane interposed between the cathode and the anode,
wherein at least one of the cathode and the anode comprises a catalyst layer comprising the polymer of claim 9.

26. A fuel cell comprising: a cathode; an anode; and an electrolyte membrane interposed between the cathode and the anode,
wherein the electrolyte membrane comprises the polymer of claim 9.

* * * * *